United States Patent
Felder et al.

(10) Patent No.: US 9,708,664 B2
(45) Date of Patent: Jul. 18, 2017

(54) COMPOSITIONS AND METHODS FOR IDENTIFYING AND DIAGNOSING SALT SENSITIVITY OF BLOOD PRESSURE

(71) Applicant: University of Virginia Patent Foundation, Charlottesville, VA (US)

(72) Inventors: Robin A. Felder, Charlottesville, VA (US); Robert M. Carey, Charlottesville, VA (US); John E. Jones, Gaithersburg, MD (US); Pedro A. Jose, Lorton, VA (US); Scott M. Williams, Hanover, NH (US)

(73) Assignee: University of Virginia Patent Foundation, Charlottesville, VA (US)

( * ) Notice: Subject to any disclaimer, the term of this patent is extended or adjusted under 35 U.S.C. 154(b) by 157 days.

(21) Appl. No.: 14/395,596

(22) PCT Filed: Apr. 22, 2013

(86) PCT No.: PCT/US2013/037557
§ 371 (c)(1),
(2) Date: Oct. 20, 2014

(87) PCT Pub. No.: WO2013/159085
PCT Pub. Date: Oct. 24, 2013

(65) Prior Publication Data
US 2015/0133414 A1 May 14, 2015

Related U.S. Application Data

(60) Provisional application No. 61/636,576, filed on Apr. 20, 2012.

(51) Int. Cl.
*C12Q 1/68* (2006.01)
*G01N 33/68* (2006.01)
*G01N 33/84* (2006.01)
*A23L 33/00* (2016.01)

(52) U.S. Cl.
CPC ............ *C12Q 1/6883* (2013.01); *A23L 33/30* (2016.08); *G01N 33/6893* (2013.01); *G01N 33/84* (2013.01); *A23V 2002/00* (2013.01); *C12Q 2600/118* (2013.01); *C12Q 2600/156* (2013.01); *G01N 2800/321* (2013.01)

(58) Field of Classification Search
None
See application file for complete search history.

(56) References Cited

U.S. PATENT DOCUMENTS

2013/0012408 A1   1/2013   Kinoshita et al.

FOREIGN PATENT DOCUMENTS

WO   WO2008109110   9/2008

OTHER PUBLICATIONS

Sanada et al, Clin. Chem. 52 (3), 352 (2006).*
Iwai et al, Hypertension 49: 825 92007).*
Pamies-Andreau et al, J. Human Hypertension 17 (3), 187 (2003).*
Felder, R., et al., "Diagnostic tools for hypertension and salt sensitivity testing", Current Opinion Nephrol. Hypertens. 2013, 22:65-76.
Weinberger, M.H., et al., "Salt sensitivity, pulse pressure, and death in normal and hypertensive humans", Hypertension 2001; 37 (2 Part 2): 429-432.
Frisoli, T.M., et al., "Salt and hypertension: is salt dietary reduction worth the effort?", Am. J. Med. 2012; 125:433-439.
Sullivan, J.M., "Salt sensitivity. Definition, conception, methodology, and long-term issues", Hypertension 1991; 17 (1 Suppl): I-61-I-68.
De la Sierra, A., et al., "Lack of correlation between two methods for the assessment of salt sensitivity in essential hypertension". J. Hum. Hypertens. 2002; 16:255-260.
Yatabe, M.S., et al., "Salt sensitivity is associated with insulin resistance, sympathetic overactivity, and decreased suppression of circulating renin activity in lean patients with essential hypertension", Am. J. Clin. Nutr. 2010; 92:77-82.
Nichols, J., et al., "Lack of validation of a same-day outpatient protocol for determination of salt sensitivity of blood pressure", Hypertension 2012; 59:390-394.
Rhee, et al., "Novel genetic variations associated with salt sensitivity in the Korean population", Hypertension Research, 2011, vol. 34, 606-611.
Agarwal, et al., "Genetics of human hypertension", Trends in Endocrinology & Metabolism, 2005, vol. 16, Issue 3, 127-133.
Zeng, et al., "The dopaminergic system in hypertension", Clinical Science, 2007, vol. 112, 583-597.
Carey, et al., "Salt sensitivity of blood pressure is associated with polymorphisms in the sodium-bicarbonate cotransporter novelty and significance", Hypertension, 2012 (published online Sep. 17, 2012, vol. 60, 1359-1366. See Abstract: pp. 1359-1364; Tables 4, 5.
Gildea, J., et al., "A linear relationship between the ex-vivo sodium mediated expression of two sodium regulatory pathways as a surrogate marker of salt sensitivity of blood pressure in exfoliated human renal proximal tubule cells: The virtual renal biopsy", Clinica Chimica Acta 421 (2013), 236-242.

(Continued)

*Primary Examiner* — James Martinell
(74) *Attorney, Agent, or Firm* — Rodney L. Sparks

(57) ABSTRACT

It was determined whether SNPs in SLC4A5 are associated with salt sensitivity of blood pressure (BP). Subjects consumed an isocaloric constant diet with a randomized order of 7 days low $Na^+$ (10 mmol/d) and 7 days high $Na^+$ (300 mmol/d) intake. Salt sensitivity was defined as a ≥7 mm Hg increase in mean arterial pressure (MAP). 35 polymorphisms in 17 candidate genes were assayed. Association analyses with salt sensitivity revealed three variants that associated with salt sensitivity, two in SLC4A5 (rs7571842, rs10177833; P<0.001), and one in GRK4 (rs1801058; P=0.020). Paradoxical changes in blood pressure in response to changes in salt intake were also found associated with a SNP for DRD2 (rs6276). In conclusion, SLC4A5 variants are strongly associated with salt sensitivity of BP in Caucasian and a DRD2 SNP is a marker for paradoxical response to salt intake.

26 Claims, No Drawings

(56) References Cited

OTHER PUBLICATIONS

Williams, J., et al., "CYP4A11 T8590C polymorphism, salt-sensitive hypertension, and renal blood flow", J. Hypertens, Oct. 2011: 29(10) 1913-1918. doi: 10.1097/HJH.0b013e32834aa786.

Uzu, T., et al., "Enhanced sodium sensitivity and disturbed circadian rhythm of blood pressure in essential hypertension", Journal of Hypertension 2006, 24: 1627-1632.

Simonetti, G., et al., "Nocturnal dipping behaviour in normotensive white children and young adults in response to changes in salt intake", Journal of Hypertension 2010, 28: 1027-1033.

Stutz, A., et al., "Functional identification of the promoter of SLC4A5, a gene associated with cardiovascular and metabolic phenotypes in the Heritage Family Study", EU Journal of Human Genetics, 2009, 17, 1481-1489.

Barkley, R., et al., "Positional Identification of Hypertension Susceptibility Genes on Chromosome 2", Hypertension, 2004; 43 [part 2]: 477-482.

Hunt, S., et al., "Sodium Bicarbonate Cotransporter Polymorphisms Are Associated With Baselilne and 10-Year Follow-Up Blood Pressures", Hypertension, 2006, 47:532-536: originally published online Dec. 19, 2005.

Yang, H., et al., "Identification of IGF1, SLC4A4, WWOX, and SFMBT1 as Hypertension Susceptibility Genes in Han Chinese with a Genome-Wide Gene-Based Association Study", PLoS One, Mar. 2012, vol. 7, Issue 3, e32907, p. 1-14.

Bengra, C., et al., "Genotyping of Essential Hypertension Single-Nucleotide Polymorphisms by a Homogeneous PCR Method with Universal Energy Transfer Primers", Clinical Chemistry 48:12, 2002, 2131-2140.

Taylor, J., et al., "Genetic and Environmental Risks for High Blood Pressure Among African American Mothers and Daughters", Biol. Res. Nurs. Jul. 2009: 11(1): 53-65.

Groger, N., et al., "Targeted mutation of SLC4A5 induces arterial hypertension and renal metabolic acidosis", Human Molecular Genetics, 2011, 1-12.

\* cited by examiner

COMPOSITIONS AND METHODS FOR IDENTIFYING AND DIAGNOSING SALT SENSITIVITY OF BLOOD PRESSURE

CROSS REFERENCE TO RELATED APPLICATIONS

This application is a national stage filing of International Application No. PCT/US2013/037557 filed Apr. 22, 2013, which is entitled to priority pursuant to 35 U.S.C. §119(e) to U.S. provisional patent application No. 61/636,576, filed on Apr. 20, 2012. The entire disclosures of the afore-mentioned patent applications are incorporated herein by reference.

STATEMENT REGARDING FEDERALLY SPONSORED RESEARCH OR DEVELOPMENT

This invention was made with government support under Grant Nos. HL074940 and HL092196, awarded by The National Institutes of Health. The government has certain rights in the invention.

BACKGROUND

Salt sensitivity is defined as a quantitative trait in which an increase in sodium ($Na^+$) load leads to an increase in blood pressure (BP). While universal consensus does not exist on the exact quantity of the $Na^+$ load, magnitude of the pressure increase or the specific protocol details required for this designation, the presence of salt sensitivity is clearly associated with an increased prevalence of cardiovascular events and mortality, irrespective of unchallenged BP levels. Indeed, normotensive (NT), yet salt-sensitive (SS) individuals have a cumulative mortality rate similar to that of hypertensive (HT) patients. In addition, SS individuals, even those with normal BP levels when initially studied, have a greater age-related increase in BP. Overall, salt sensitivity has been estimated to be present in 51% of hypertensive and 26% of normotensive subjects, posing a major public health problem in the United States and other Westernized societies.

The underlying pathophysiological mechanisms of salt sensitivity are currently unknown. However, there is strong evidence that genetic mechanisms may underlie variations in the BP response to dietary salt intake. In particular, there is tight maternal-offspring association of BP change with dietary $Na^+$ restriction. Salt sensitivity, hypertension and related cardiovascular diseases are thought to result from the interaction of genes with the environment (e.g., stress and diet), but the specific genes involved in susceptibility to salt sensitivity have not been completely clarified.

The $Na^+$-bicarbonate co-transporter gene (SLC4A5) on chromosome 2 encodes a protein that transports $Na^+$ and $HCO_3^-$ electrogenically across the basolateral membranes of many cell types, including renal tubule cells, into the interstitial fluid and ultimately into the circulation. SNPs of SLC4A5 have been associated with baseline and 10-year follow-up BP in previous studies. Additionally, targeted mutation of SLC4A5 has been found to induce arterial hypertension in mice (Groger et al., 2012).

There is a long felt need in the art for compositions and methods useful for identifying, diagnosing, treating, and monitoring subjects with salt sensitivity of blood pressure. The present invention satisfies these needs.

SUMMARY OF THE INVENTION

The present application discloses single nucleotide polymorphisms (SNPs) that are associated with salt sensitivity of blood pressure and paradoxical responses to level of sodium intake. The present application discloses that single nucleotide polymorphisms (SNPs) in several genes, but especially the sodium-bicarbonate co-transporter, SLC4A5, are associated with, or are markers for, salt sensitivity of blood pressure. The data disclosed are based on studies in two Caucasian populations.

The present application further discloses unexpected results where a SNP is an indication of a subject who demonstrates an increase in blood pressure on a low salt diet. The present application further discloses the unexpected result of a SNP being an indication of a subject's susceptibility to decrease in BP when on a high salt diet or after increased salt intake.

It is disclosed herein that there is an association of SLC4A5 SNPs with salt sensitivity of BP, and that other SNPs may also be associated with salt sensitivity of BP, including G protein-coupled kinase receptor 4 (GRK4).

It is also disclosed herein that the presence of a variant in dopamine type 2 receptor (DRD2) is associated with, or indicative of, a paradoxical increase in BP in some subjects when on a low salt diet or of subjects with a paradoxical decrease in BP on a high salt diet.

It is disclosed herein that the genotypes of hypertensive and normotensive subjects do not indicate whether they are salt sensitive or salt resistant or will have a paradoxical response to either a high level or reduced level of sodium intake.

The present invention provides compositions and methods useful for identifying, detecting, and diagnosing salt sensitivity based on variations found in genes that are identified herein to be associated with salt sensitivity. These variations are useful as markers for salt sensitivity. In one aspect, the salt sensitivity is salt sensitivity of blood pressure. The present invention therefore encompasses compositions and methods for identifying, detecting, diagnosing, and monitoring the progression and treatment of subjects with salt sensitivity or hypertension. In one aspect, the salt sensitivity is independent of hypertension. In one aspect, the increase in blood pressure is $\geq 7$ mm Hg. In another aspect, it is $\geq 10$ mm Hg.

In one aspect, a diagnosis or determination is based on detection or measurement of nucleotide polymorphisms. In one aspect, a polymorphism is a single nucleotide polymorphism (SNP).

In one aspect, the present invention provides a panel of genes and SNPs useful for identifying and diagnosing salt sensitivity of blood pressure in response to dietary sodium. In one aspect, one SNP can be used. In another aspect, two or more SNPs are used in combination. In another aspect, three or more SNPs can be used. In one aspect, the one or more SNPs are selected from the Tables provided herein. The present invention provides for the use of panels of variants and SNPs as part of a diagnosis or for preparing a strategy for treatment based on variants found.

In one embodiment, a combination of up to 35 polymorphisms are used to determine blood pressure sensitivity to salt. In one aspect, a combination of more than 35 polymorphisms are used. In one aspect, polymorphisms of up to 17 genes are used to determine blood pressure sensitivity to salt. In another aspect, polymorphisms of more than 17 genes can be used. One of skill in the art will appreciate that the combinations can be varied.

In one embodiment, single nucleotide polymorphisms of one or more of the 17 genes of Table S3 are analyzed in an assay to determine salt sensitivity of blood pressure. The genes of Table S3 are CYP11β2, ADD1, AGT, AGTR1, ACE, CAV, CCKAR, CCKBR, CYP4A11, DRD2, GRK4, eNOS, PPP2R2C, SLC4A5, SNX1, SNX5, and SNX19. In one aspect, single nucleotide polymorphisms of two or more genes are used. In another aspect, single nucleotide polymorphisms of three or more genes are used. In yet another aspect, single nucleotide polymorphisms of four or more genes are used. In a further aspect, single nucleotide polymorphisms of five or more genes are used. In one aspect, at least two single nucleotide polymorphisms are examined. In one aspect, at least three single nucleotide polymorphisms are examined. In one aspect, at least four single nucleotide polymorphisms are examined. In one aspect, at least five single nucleotide polymorphisms are examined. The single nucleotide polymorphisms of Table S3 are rs1799998, rs4961, rs1541582, rs699, rs5186, rs1799752, rs3807990, rs3840634, rs41267457, rs1805000, rs1805002, rs1126742, rs1799732, rs1800497, rs1079597, rs6276, rs2960306, rs1024323, rs1801058, rs1799983, rs35368770, rs35410672, rs3796403, rs11545013, rs7571842, rs10177833, rs1130604, rs1802376, rs34910981, rs6045116, rs3751037, rs3190345, rs681982, rs4414223, and rs2298566. Accordingly, the invention provides methods of determining a susceptibility to salt sensitivity in a subject. In one aspect, the sensitivity is salt sensitivity of blood pressure. In a specific embodiment, the method comprises obtaining sequence data about a subject identifying at least one allele of at least one polymorphic marker selected from the group consisting of: rs1799998, rs4961, rs1541582, rs699, rs5186, rs1799752, rs3807990, rs3840634, rs41267457, rs1805000, rs1805002, rs1126742, rs1799732, rs1800497, rs1079597, rs6276, rs2960306, rs1024323, rs1801058, rs1799983, rs35368770, rs35410672, rs3796403, rs11545013, rs7571842, rs10177833, rs1130604, rs1802376, rs34910981, rs6045116, rs3751037, rs3190345, rs681982, rs4414223, and rs2298566.

In one embodiment, three SNPs are associated with salt sensitivity of blood pressure. In one aspect, the SNPs are SLC4A5 and GRK4 SNPs. In one aspect, the variants are SLC4A5 SNP rs7571842, SLC4A5 SNP rs10177833, and GRK4 SNP rs1801058.

In one embodiment, identification of a SLC4A5 SNP in a subject is an indication of salt sensitivity of blood pressure. In one aspect, the association with salt sensitivity is in a Caucasian. In another aspect, it is known that those of African American descent have an increased susceptibility to salt sensitivity of blood pressure.

In one embodiment, at least one SNP is a SLC4A5 SNP. In one aspect, the SLC4A5 SNP is rs7571842. In one aspect, a G allele confers protection against salt sensitivity of blood pressure. In one aspect, an A allele indicates an increased salt sensitivity of blood pressure. In one aspect, a subject has salt sensitivity of blood pressure when the SLC4A5 gene had the AA or GA genotype of rs7571842.

In one aspect, the SLC4A5 SNP is rs10177833. In one aspect, a C allele is protective. In one aspect, an A allele indicates an increased salt sensitivity of blood pressure.

In one aspect, at least two SLC4A5 SNPs are used in the diagnosis.

In one embodiment, a SNP is a GRK4 SNP. In one aspect, the GRK4 SNP is rs1801058.

In one embodiment, a salt sensitive subject is one who has about a ≥7 mm Hg increase in mean arterial pressure ("MAP") when tested during a transition between a high and low sodium diet or who has such a change when consuming sodium. In one aspect, the increase is ≥10 mm Hg.

In one embodiment, the association remains significant even after adjustment for criteria such as body mass index ("BMI") or age.

In one aspect, sensitivity is tested by varying the sodium intake and then assaying BP and other criteria disclosed herein or known in the art and comparing with the results of the biomarker studies.

The present application discloses two unexpected results for the dopamine type 2 receptor SNP rs6276 (see Tables 2, 3A, S2, and S3).

In one embodiment, the present invention provides compositions and methods useful for identifying, detecting, diagnosing, and monitoring the progression and treatment of subjects who demonstrate an increase in BP even when on a low salt diet. In one aspect, a variation of a SNP in the dopamine type 2 receptor is an indication that the subject is susceptible to or will demonstrate an increase in BP on a low salt diet. In one aspect, the association is with the SNP rs6276. In one aspect, an A allele is indicative of salt sensitivity.

Additionally, based on the unexpected result disclosed herein regarding a group of subjects showing decreases in MAP upon salt loading or intake, the present invention further provides compositions and methods useful for identifying, detecting, diagnosing, and monitoring the progression and treatment of subjects who demonstrate a decrease in BP when on a high salt diet or after increased salt intake and an increase in blood pressure on a low salt intake. Each subject expresses a "personal salt index" that is associated with the presence of SNPs in metabolic pathways. In one aspect, a variation in the dopamine type 2 receptor is an indication that the subject is susceptible to or will demonstrate a decrease in BP on a high salt diet. In one aspect, the association is with the SNP rs6276. A negative response to salt loading is a decrease of MAP upon high sodium intake. It is disclosed herein that the dopamine type 2 receptor SNP rs6276 is associated with a decrease in MAP, and is therefore negatively associated with salt sensitivity. In one aspect, it is negatively associated with salt sensitivity in white subjects (Caucasians). Therefore, the present application discloses two separate associations for the dopamine type 2 receptor SNP rs6276. First, SNP rs6276 is positively associated with an increase in BP in subjects who demonstrate an increase in BP even when on a low salt diet. Second, SNP rs6276 is negatively associated with salt sensitivity of BP in Caucasians (whites).

In one aspect, a sample from said subject is analyzed. One of ordinary skill in the art will appreciate that useful samples may vary. For example, useful samples of the invention can include, but are not limited to, normal tissue samples, diseased tissue samples, sputum, mucus, phlegm, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, exosomes, and urine. In one aspect, the urine comprises exfoliated cells. In one aspect, the cells and tissues are living. In one aspect, a sample comprises nucleic acid. In one aspect, nucleic acid obtained from urine is in soluble form. In another aspect, the urine comprises exosomes secreted from renal cells. In one aspect, the exosomes comprise nucleic acid.

The present invention further provides compositions and methods useful for identifying, detecting, diagnosing, and monitoring the progression and treatment of subjects who demonstrate a decrease in BP even when on a high salt diet.

There is currently no diagnostic test for these individuals who have a paradoxical increase in blood pressure on a low salt diet. The present invention therefore encompasses such a diagnostic test. The present invention further encompasses the use of said compositions and methods to provide each individual with a "personal salt index", which is defined as the maximum amount of daily/weekly/or monthly salt intake into the diet that will reduce the likelihood of the individual developing salt associated illnesses.

The present invention further encompasses the reporting of the predisposition to develop salt-related illnesses, including, but not limited to, stroke, blindness, kidney disease, and heart attack through the use of the described diagnostic inventions. The present invention further encompasses combining or selecting treatment regimens based on the results of the assays disclosed herein. One embodiment provides for a method of predicting a response to treatment for a disorder related to salt sensitivity in a subject. The invention further provides for the use of combinations of assays to help further predict a predisposition to or having salt sensitivity and to help predict treatments based on the results of the assays. In one aspect, treatments include a subject reducing their daily, weekly, or monthly salt consumption below the level of their personal salt index as predicted by the presence of at least one predictive single nucleotide polymorphism or selected combinations of predictive single nucleotide polymorphisms. In one aspect, at least one drug or agent which regulates blood pressure is administered to the subject. In another aspect, combination therapy can be used by administering additional drugs. In one aspect, the treatment includes modification of salt intake and/or diet modification. In one aspect, the treatment includes a combination of treatment with drugs and a modification of salt intake and/or diet modification. Treatments are based on many factors, including, but not limited to, genetic and environmental factors and include diet quality, age, body mass, and race/ethnicity. Useful drugs, include, but are not limited to, diuretics, mineralocorticoid receptor antagonists, combination diuretics, beta-blockers, alpha-blockers, angiotensin-converting enzyme inhibitors, angiotensin II receptor blockers, calcium channel blockers, central agonists, peripheral acting adrenergic blockers, direct vasodilators, and direct renin inhibitors, and combinations thereof.

The polymorphisms identified herein, where appropriate, can also include their related miRNA, mRNA, ncRNA, or protein expression, levels, or states of function, or other biochemical products or chemical associations, which may serve as biomarkers.

In one embodiment, a sample is obtained from a subject. In one aspect, the sample is processed and subjected to nucleotide sequence measuring technologies to detect and identify a marker of the invention. In one aspect, the marker is associated with salt sensitivity. In one aspect, more than one marker (variation/SNP) is used. In one aspect, the resulting data is quantified or summarized with an analytical device and program. In one aspect, detection comprises analyzing the results with an analytical device and program. In one aspect, the analytical device is a computer.

The present invention further provides compositions and methods useful for personalized medicine.

The present invention further provides for advice to be provided to subjects in conjunction with a modified diet and/or drug therapy. Advice constitutes a set of instructions pertaining to the potential consequences of excessive salt intake above each individual's "personal salt index", especially for subjects with low levels of the continuous variable of a personal salt index, or of low salt intake in the case of subjects exhibiting the paradoxical increase in blood pressure on a low salt diet which would be determined to have a high personal salt index. Any of these strategies either alone or in any combination, and no matter how brief or lengthy, can constitute advice. The advice can be provided in a format such as written, electronic, or interpersonal. In one embodiment, the drug combination therapy is more effective at treatment or prevention than merely administering a placebo and providing advice, administering no drugs and providing advice, or not administering drugs or providing advice. In one aspect, the combination drug therapy is more effective at treatment or prevention than drug therapy used in combination with a psychosocial management program.

Based on the results disclosed herein, the various diagnostics can be used to help predict what types of therapy will be useful, or potentially harmful, to a subject. For example, in a subject where a SNP associated with a propensity to develop increased blood pressure on a low salt diet has been found, then a treatment regimen would be established to take into account the negative results of a low salt diet, perhaps by avoiding a low salt diet, and by the use of medication to control the blood pressure. Additionally, in a subject where a SNP has been found that has a negative association or response to salt loading, resulting in a decrease in blood pressure, a treatment regimen can be established to control sodium uptake and drugs chosen to control blood pressure and to try and prevent a decrease in blood pressure upon intake of salt. In one aspect, the present invention provides methods for selecting subjects who will be responsive to particular treatment regimen based on the SNPs identified in the subjects.

In one embodiment, a compound being administered is administered at least once a day. In one aspect, it is administered at least twice a day. In another embodiment, it is administered at least once a week. In yet another embodiment, it is administered at least once a month.

The invention further provides kits for diagnosing, detecting, and monitoring a subject's personal salt index and treating the subject's relative salt sensitivity associated with a marker of the invention.

Various aspects and embodiments of the invention are described in further detail below.

DETAILED DESCRIPTION

Abbreviations and Acronyms

20-HETE—20-hydroxyeicosatetraenoic acid
ACE—angiotensin converting enzyme
ACEI—angiotensin converting enzyme inhibitors
ADD—alpha adducin
ADD1—alpha adducin 1
ADD2—alpha adducin 2
AGT—angiotensinogen
AGTR1—angiotensin II receptor Type I
ARB—angiotensin receptor blockers
ASO—allele-specific oligonucleotide
AS-PCR—allele specific PCR
BMI—body mass index
BP—blood pressure
C allele—cytosine allele
CAV1—caveolin 1
CC genotype—homozygous for cytosine on each of two inherited alleles
CCKAR—cholecystokinin A receptor
CCKBR—cholecystokinin B receptor CT genotype—heterozygous, with one cytosine and one thymidine allele
CYP11β2—aldosterone synthase
CYP4A11—cytochrome P450-4A11
DRD2—dopamine $D_2$ receptor, also referred to as D2R, D2DR, dopamine type 2 receptor and dopamine receptor $D_2$
EETs—epoxyeicosatrienoic acids
eNOS—nitric oxide synthase 3 (endothelial cell)
G allele—guanine allele
GG genotype—homozygous for guanine on each of two inherited alleles
GRK4—G protein-coupled receptor kinase 4
GWAS—genome-wide association studies
HS—high sodium
HT—hypertensive
HWE—Hardy-Weinberg equilibrium
HyperPATH—hypertension pathotype
LD—linkage disequilibrium
LNA—locked nucleic acid
LS—low sodium
MAP—mean arterial pressure
mm—millimeters
NCBI—National Center for Biotechnology Information
ncRNA—noncoding RNA
NT—normotensive
OR—odds ratio
PASA—PCR amplification of specific alleles
PNA—peptide nucleic acid
PPP2R2C—protein phosphatase 2, regulatory subunit B, gamma isoform
PRC—in-patient research center
RR—relative risk
SLC4A5—sodium-bicarbonate co-transporter gene, member 5, also referred to as N+-bicarbonate co-transporter
SNP—single nucleotide polymorphism
SNX1—sorting nexin 1
SNX19—sorting nexin 19
SNX5—sorting nexin 5
SR—salt resistant
SS—salt sensitive
SSCP—single stranded conformation polymorphism assays
T allele—thymidine allele
tagSNP—tagging SNPs
TT genotype—homozygous for thymidine on each of two inherited alleles Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

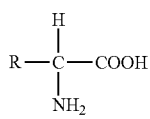

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, sputum, mucus, phlegm, tissues, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. One of skill in the art will understand the type of sample needed.

A "biomarker" or "marker" is a specific biochemical in the body which has a particular molecular feature that makes it useful for measuring the progress of disease or the effects of treatment, or for measuring a process of interest.

As used herein, the term "carrier molecule" refers to any molecule that is chemically conjugated to the antigen of interest that enables an immune response resulting in antibodies specific to the native antigen.

The term "cell surface protein" means a protein found where at least part of the protein is exposed at the outer aspect of the cell membrane. Examples include growth factor receptors.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

A "computer-readable medium" is an information storage medium that can be accessed by a computer using a commercially available or custom-made interface. Exemplary compute-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "nasal administration" in all its grammatical forms refers to administration of at least one compound of the invention through the nasal mucous membrane to the bloodstream for systemic delivery of at least one compound of the invention. The advantages of nasal administration for delivery are that it does not require injection using a syringe and needle, it avoids necrosis that can accompany intramuscular administration of drugs, and trans-mucosal administration of a drug is highly amenable to self-administration.

The term "negative response" to salt loading means a decrease in MAP upon sodium intake, particularly high sodium intake.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Obesity" is commonly referred to as a condition of increased body weight due to excessive fat. Drugs to treat obesity are generally divided into three groups: (1) those that decrease food intake, such as drugs that interfere with monoamine receptors, such as noradrenergic receptors, serotonin receptors, dopamine receptors, and histamine receptors; (2) those that increase metabolism; and (3) those that increase thermogenesis or decrease fat absorption by inhibiting pancreatic lipase (Bray, 2000, Nutrition, 16:953-960 and Leonhardt et al., 1999, Eur. J. Nutr., 38:1-13). Obesity has been defined in terms of body mass index (BMI). BMI is calculated as weight (kg)/[height (m)]$^2$, according to the guidelines of the U.S. Centers for Disease Control and Prevention (CDC), and the World Health Organization (WHO). Physical status: The use and interpretation of anthropometry. Geneva, Switzerland: World Health Organization 1995. WHO Technical Report Series), for adults over 20 years old, BMI falls into one of these categories: below 18.5 is considered underweight, 18.5-24.9 is considered normal, 25.0-29.9 is considered overweight, and 30.0 and above is considered obese.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof "Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl.

See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

The term "salt sensitivity of blood pressure" is a quantitative trait in which an increase in sodium (Na+) load leads to an increase in blood pressure (BP)

A "sample," as used herein, refers preferably to a biological sample from a subject for which an assay or other use is needed, including, but not limited to, normal tissue samples, diseased tissue samples, sputum, mucus, phlegm, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. A sample can also be any other source of material obtained from a subject which contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function.

Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

A "variant", as described herein, refers to a segment of DNA that differs from the reference DNA. A "marker" or a "polymorphic marker", as defined herein, is a variant. Alleles that differ from the reference are referred to as "variant" alleles.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like.

Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

Past studies have demonstrated that single nucleotide polymorphisms (SNPs) of the sodium-bicarbonate co-transporter gene (SLC4A5) are associated with hypertension. The present application tested the hypothesis that SNPs in SLC4A5 are associated with salt sensitivity of blood pressure (BP). To that end, described herein are studies that were performed in 185 Caucasians consuming an isocaloric constant diet with a randomized order of 7 days low Na+ (10 mEq/d) and 7 days high Na+ (300 mEq/d) intake. Salt sensitivity was defined as a ≥7 mm Hg increase in mean arterial pressure (MAP) during a randomized transition between high and low Na+ diet.

Generally, salt sensitivity of blood pressure is a quantitative trait in which an increase in sodium (Na+) load leads to an increase in blood pressure (BP). In one aspect, salt sensitivity is about a ≥7 mm Hg increase in mean arterial pressure (MAP) during a randomized transition between high and low Na+ diet.

The subjects studied herein were classified either as normotensive (NT; BP<140 SBP and <90 DBP mm Hg) or hypertensive (HT; history of prior diagnosis of hypertension or diastolic BP 90-114 mm Hg following a 3-week withdrawal from all antihypertensive medications or average BP readings during the pre-study screening period ≥140/90 mm Hg).

A total of 35 polymorphisms in 17 candidate genes were assayed, 25 of which were tested for association. Association analyses with hypertension at baseline revealed only two associations, rs4961 in alpha adducin (P=0.027) and G protein-coupled receptor kinase-4 (GRK4) SNP rs1801058 (p=0.018). Both of these remained nominally significant in logistic regression models after adjusting for covariates (p<0.02 for both).

Association analyses with salt sensitivity revealed three variants that associated with salt sensitivity, two in SLC4A5 (p<0.001), and one in GRK4 (P-=0.020). Of these, two SNPs in SLC4A5 (rs7571842 and rs10177833) demonstrated highly significant results and large effects sizes, using logistic regression. These two SNPs had P values of $2.9 \times 10^{-5}$ and $2.9 \times 10^{-4}$ with odds ratios of 5.6 and 5.0 in unadjusted regression models, respectively. These SNPs remained significant after adjusting for BMI and age, (P=$2.4 \times 10^{-4}$ and $1.9 \times 10^{-4}$ and odds ratios 4.8 and 5.4, respectively). These two SLC4A5 SNPs were in linkage disequilibrium (LD) in both salt sensitive (SS) and salt resistant (SR) subjects, but the strength of the LD was greater in SR subjects, (r2=0.61 and 0.93, respectively), further supporting the conclusion of an association of SLC4A5 with salt sensitivity.

The present application discloses that SLC4A5 variants are strongly associated with salt sensitivity. In one aspect, the salt sensitivity is in Caucasians.

SLC4A5 (Homo sapiens solute carrier family 4, sodium-bicarbonate co-transporter) has NCBI Reference Sequence Number NG_032663.1 and is 134,166 bp DNA. There are 2095 SNPs in SLC4A5. SNPs rs7571842 and rs10177833 are both located in the intron region having Ref. Seq. No. NM_021196.3.

rs7571842 has a single nucleotide variation and the reference/SNP alleles are A/G, the ancestral allele being G. The position on chromosome 2 is 74460904(+).

rs10177833 has a single nucleotide variation and the reference/SNP allele is A/C, the ancestral allele being C. The position on chromosome 2 is 74457718 (+).

With regard to identifying and measuring polymorphisms of a gene associated with salt sensitivity herein for diagnostic and monitoring purposes, the present invention further provides for measuring and comparing SLC4A5 expression, levels, and activity in subjects with varying genotypes to predict predilection to salt sensitivity, to establish treatment regimens based on the diagnostic assays measuring the polymorphisms and/or SLC4A5 expression levels, and activity which help determine which subjects are amenable to particular treatment regimens, as well as to monitor the progression of the treatment.

The present invention encompasses the use of at least one SNP for G protein could receptor kinase 4 (GRK4). GRK4 is located on chromosome 4 (4p16.3) and its NCBI Reference Seq. No. is NC_000004.11. The chromosome position of GRK4 SNP rs1801058 is 3039150. The amino acid position is 454.

The present invention encompasses the use of least one SNP for dopamine type 2 receptor. The dopamine type 2 receptor gene is located on chromosome 11. The NCBI Reference Sequence No. is NG_008841.1 (72685 bp DNA). In one aspect, a dopamine type 2 receptor SNP of the invention is SNP rs6276. The chromosome 11 position of the SNP is 113281397(−). There are two mRNA variants (NM 000795.3 and NM_016574.3).

SNPs can be detected using methods described herein or that are known in the art (see Sanada et al., 2006, Clin. Chem., 52:352-360), for example by fluorescence probe melting curves. A SNP can be genotyped using a fluorescent allele-specific polymerase chain reaction (PCR)-based assay. In one embodiment, a SNP can be identified and genotyped by at least one method selected from the group consisting of hybridization by microarrays, allele-specific probe hybridization, allele-specific amplification, sequencing, 5' nuclease digestion, molecular beacon assay, oligonucleotide ligation assay, size analysis, and single-stranded conformation polymorphism.

In one embodiment, the present invention encompasses compositions and methods useful for identifying a genetic predisposition for salt sensitivity of blood pressure. The present application discloses genes with at least one risk allele in specific single nucleotide polymorphism sites that are associated with salt sensitivity of blood pressure, and unexpectedly the sensitivity can occur in hypertensive and normotensive subjects, because the present application demonstrates that the blood pressure response to salt in the diet is a continuous variable and is determine by an individual's personal salt index. The invention encompasses obtaining a sample from a test subject, wherein the sample comprises nucleic acids, analyzing the sample for the presence of one or more single nucleotide polymorphisms associated with salt sensitivity of blood pressure, wherein the presence of one or more of the risk alleles in the single nucleotide polymorphism associated with salt sensitivity of blood pressure, is an indication of a predisposition or increased risk for salt sensitivity of blood pressure. In one aspect, the predisposition may have already been manifested in the subject. The risk allele nucleotide residue is at a specific position on the chromosome. The single nucleotide polymorphisms are identified by name and the residue position of the single nucleotide is known in the art.

In one embodiment, the present invention encompasses diagnosing salt sensitivity of blood pressure or paradoxical responses to salt intake comprising determining the presence or absence of a polymorphic allele in a biological sample from a test subject, wherein at least one polymorphic allele of risk is genetically linked to one or more of the genes of Table S2, and wherein the presence of the allele is indicative of a salt sensitivity of blood pressure or a paradoxical response to salt intake. In one aspect, the polymorphic allele comprises a single nucleotide polymorphism. In one aspect, the results of the diagnostic tests can be used for guidance in developing a treatment strategy for a subject who is diagnosed with salt sensitivity of blood pressure or paradoxical responses to salt intake.

In one embodiment, the association of a SNP remains significant even after adjusting for BMI and age.

In one embodiment, the invention provides for a method of determining the existence of salt sensitivity of blood pressure or a paradoxical response to salt intake comprising analyzing a sample from at test subject for the presence or absence of an known allele of at least one SNP of Table S3, wherein said SNP is associated with salt sensitivity of blood pressure or a paradoxical response to salt intake. In one aspect, nucleic acid from the sample is analyzed. In one aspect, the nucleic acid is sequenced. In one aspect, the sample is a biological sample obtained from the subject. In one aspect, the sample is exfoliated renal proximal tubule cells isolated from urine excreted by the subject in which the exfoliated cells are tested for their ability to respond to a sodium challenge. In one aspect, sequence is compared to a database containing correlation data between polymorphic markers and the existence of, or susceptibility to, salt sensitivity of blood pressure and/or a paradoxical response to salt intake. In one aspect, the paradoxical response to salt is an increase in blood pressure when on a low sodium diet. In another aspect, the paradoxical response to salt is a decrease in blood pressure upon high sodium intake. In one aspect, relative risk or odds ratios are calculated. In one aspect, the odds ratio is at least about 0.2, or at least about 0.5, or at least about 1.0, or at least about 1.5. In one aspect, the data obtained can be reported to at least one entity selected from the group consisting of a subject, a guardian of the subject, a genetic service provider, a physician, a medical organization, and a medical insurer.

In one aspect, the data can be used to determine a lack of salt sensitivity of blood pressure or lack of paradoxical response to salt intake. In one aspect, the sensitivity determination is performed using a computer-readable medium having computer executable instructions for determining the existence of or predilection to/susceptibility to the sensitivity, the computer readable medium comprising: allelic frequency data indicative of at least one polymorphic marker; a routine stored on the computer readable medium and adapted to be executed by a processor to determine the existence of or a predilection to/susceptibility to salt sensitivity of blood pressure or paradoxical response to salt intake based on the data for at least on of the SNPs. In one aspect, the SNPS are SNPS of Table S3. In one aspect, the at least one SNP is a SNP of SLC4A5, GRK4, or DRD2. In one aspect, the computer readable medium contains data indicative of at least two SNPs. The step of analyzing the nucleic acid can utilize any of the techniques describe herein or known in the art.

In one embodiment, the present invention provides for determining the likelihood that a subject has salt sensitivity to blood pressure and/or a paradoxical response to salt intake comprising analyzing a nucleic acid sample obtained from the subject, detecting the presences or absence of one or more variations in at least one of the genes of Table S3, and determining that the subject has, or is at risk of developing, salt sensitivity of blood pressure or a paradoxical response to salt intake, when one or more of the variations disclosed herein is detected. In one aspect, the sample comprises nucleic acid. In one aspect, the nucleic acid is amplified.

Related aspects of the invention include a screening method, genotyping methods, and prognostic methods. For example, the invention includes a method of screening a candidate marker for assessing susceptibility to a condition causative of or correlative with salt sensitivity of blood pressure. The method comprises analyzing the frequency of at least one allele of a polymorphic marker of a group further described herein in a population of subjects diagnosed with the condition, wherein a significant difference in frequency of the at least one allele in the population of subjects diagnosed with the condition as compared to the frequency of the at least one allele in a control population of subjects is indicative of the allele as a marker of the condition.

The invention also includes methods of genotyping a nucleic acid sample obtained from a subject at risk for, or diagnosed with hypertension or a condition described herein comprising determining the identity of at least one allele of at least one polymorphic marker in the sample, wherein the marker is one which associates with salt sensitivity of blood pressure, or other conditions disclosed herein, or is a marker in linkage disequilibrium therewith. With regard to the inventive genotyping methods presented herein, it should be appreciated that the methods do not provide the identification of a number of alleles such that the entire genome of the human individual is genotyped. Rather, the inventive methods provide the identification of a number, e.g., 100 or less, of alleles of the human individual.

In one embodiment, to diagnose a susceptibility to or existence of salt sensitivity of blood pressure or other condition disclosed herein, a hybridization sample can be formed by contacting the test sample containing a nucleic acid, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 10, 15, 30, 50, 100, 250, or 500 nucleotides in length that is sufficient to specifically hybridize under stringent conditions to appropriate mRNA or genomic DNA. For example, the nucleic acid probe can comprise all or a portion of the nucleotide sequence of a gene selected from the group consisting of the genes described herein, and/or a LD block of any one of these genes, as described herein, optionally comprising at least one allele of a marker described herein, or at least one haplotype described herein, or the probe can be the complementary sequence of such a sequence. In a particular embodiment, the nucleic acid probe is a portion of the nucleotide sequence of a gene selected from the above group and/or the LD block of the gene, as described herein, optionally comprising at least one allele of a marker described herein, or at least one allele of a polymorphic marker of a haplotype comprising at least one polymorphic marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, can be detected using standard methods. If specific hybridization occurs between the nucleic acid probe and the nucleic acid in the test sample, then the sample contains the allele that is complementary to the nucleotide that is present in the nucleic acid probe. The process can be repeated for any markers of the invention, or markers that make up a haplotype of the invention, or multiple probes can be used concurrently to detect more than one marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative of the source of the sample having the particular haplotype (e.g., a haplotype) and therefore is susceptible to the condition being tested.

In one embodiment, a method utilizing a detection oligonucleotide probe comprising a fluorescent moiety or group at its 3' terminus and a quencher at its 5' terminus, and an enhancer oligonucleotide, can be employed, as described by Kutyavin et al. (Nucleic Acid Res. 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic a basic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of a person of ordinary skill in the art.

In one embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In another hybridization method, Northern analysis (see Current Protocols in Molecular Biology, Ausubel et al., eds., John Wiley & Sons, supra) is used to identify the presence of a polymorphism associated with salt sensitivity of blood pressure or other conditions associated with paradoxical responses to salt intake. For Northern analysis, a test sample of RNA is obtained from the subject by appropriate means. As described herein, specific hybridization of a nucleic acid probe to RNA from the subject is indicative of a particular allele complementary to the probe. For representative examples of use of nucleic acid probes, see, for example, U.S. Pat. Nos. 5,288,611 and 4,851,330.

Additionally, or alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T, or U) attached to the glycine nitrogen via a methylene carbonyl linker (see, for example, Nielsen et al., Bioconjug. Chem. 5:3-7 (1994)). The PNA probe can be designed to specifically hybridize to a molecule in a sample suspected of containing one or more of the marker alleles or haplotypes that are associated with, for example, salt sensitivity of blood pressure or other conditions associated with paradoxical responses to salt intake. Hybridization of the PNA probe is thus diagnostic for salt sensitivity of blood pressure or other condition of the invention being analyzed.

In one embodiment of the invention, a test sample containing genomic DNA obtained from the subject is collected and the polymerase chain reaction (PCR) is used to amplify a fragment comprising one or more markers or haplotypes of the invention. As described herein, identification of a particular marker allele or haplotype associated with salt sensitivity of blood pressure can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis, for example using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s) that is encoded by a nucleic acid associated with a condition where changes in the protein sequence occur because of the change in the gene. Further, the expression of the variant(s) can be quantified as physically or functionally different.

Sequence analysis can also be used to detect specific alleles or haplotypes associated with salt sensitivity of blood pressure or other conditions associated with paradoxical responses to salt intake. Therefore, in one embodiment, determination of the presence or absence of a particular marker allele or haplotype comprises sequence analysis of a test sample of DNA or RNA obtained from a subject or individual. PCR or other appropriate methods can be used to amplify a portion of a nucleic acid associated with salt sensitivity of blood pressure or other conditions associated with paradoxical responses to salt intake and the presence of a specific allele can then be detected directly by sequencing the polymorphic site (or multiple polymorphic sites in a haplotype) of the genomic DNA in the sample.

Allele-specific oligonucleotides can also be used to detect the presence of a particular allele in a nucleic acid associated with salt sensitivity of blood pressure or other conditions associated with paradoxical responses to salt intake, through the use of dot-blot hybridization of amplified oligonucleotides with allele-specific oligonucleotide (ASO) probes (see, for example, Saiki et al., Nature 324:163-166 (1986)). An "allele-specific oligonucleotide" (also referred to herein as an "allele-specific oligonucleotide probe"), in one aspect, is an oligonucleotide of approximately 10-50 base pairs or approximately 15-30 base pairs, that specifically hybridizes to a nucleic acid associated with salt sensitivity of blood pressure or other conditions associated with paradoxical responses to salt intake and which contains a specific allele at a polymorphic site (e.g., a marker or haplotype as described herein). An allele-specific oligonucleotide probe that is specific for one or more particular a nucleic acid associated with salt sensitivity of blood pressure or other conditions associated with paradoxical responses to salt intake can be prepared using standard methods (see, e.g., Current Protocols in Molecular Biology, supra). PCR can be used to amplify the desired region. The DNA containing the amplified region can be dot-blotted using standard methods (see, e.g., Current Protocols in Molecular Biology, supra), and the blot can be contacted with the oligonucleotide probe. The presence of specific hybridization of the probe to the amplified region can then be detected. Specific hybridization of an allele-specific oligonucleotide probe to DNA from the subject is indicative of a specific allele at a polymorphic site associated with a disease (see, e.g., Gibbs et al., Nucleic Acids Res. 17:2437-2448 (1989) and WO 93/22456).

With the addition of analogs such as locked nucleic acids (LNAs), the size of primers and probes can be reduced to as few as 8 bases. LNAs are a novel class of bicyclic DNA analogs in which the 2' and 4' positions in the furanose ring are joined via an O-methylene (oxy-LNA), S-methylene (thio-LNA), or amino methylene (amino-LNA) moiety. Common to all of these LNA variants is an affinity toward complementary nucleic acids, which is by far the highest reported for a DNA analog. For example, particular all oxy-LNA nonamers have been shown to have melting temperatures (Tm) of 64° C. and 74° C. when in complex with complementary DNA or RNA, respectively, as opposed to 28° C. for both DNA and RNA for the corresponding DNA nonamer. Substantial increases in Tm are also obtained when LNA monomers are used in combination with standard DNA or RNA monomers. For primers and probes, depending on where the LNA monomers are included (e.g., the 3' end, the 5' end, or in the middle), the Tm could be increased considerably.

In another embodiment, arrays of oligonucleotide probes that are complementary to target nucleic acid sequence segments from a subject, can be used to identify polymorphisms in a nucleic acid associated with salt sensitivity of blood pressure or other conditions associated with paradoxical responses to salt intake. For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light directed synthesis methods that incorporate a combination of photolithographic methods and solid phase oligonucleotide synthesis methods, or by other methods known to the person skilled in the art (see, e.g., Bier et al., Adv Biochem Eng Biotechnol 109:433-53 (2008); Hoheisel, Nat Rev Genet. 7:200-10 (2006); Fan et al., Methods Enzymol 410:57-73 (2006); Raqoussis & Elvidge, Expert Rev Mol Diagn 6:145-52 (2006); Mockler et al., Genomics 85:1-15 (2005), and references cited therein, the entire teachings of each of which are incorporated by reference herein). Many additional descriptions of the preparation and use of oligonucleotide arrays for detection of polymorphisms can be found, for example, in U.S. Pat. No. 6,858,394, U.S. Pat. No. 6,429,027, U.S. Pat. No. 5,445,934, U.S. Pat. No. 5,700,637, U.S. Pat. No. 5,744,305, U.S. Pat. No. 5,945,334, U.S. Pat. No. 6,054,270, U.S. Pat. No. 6,300,063, U.S. Pat. No. 6,733,977, U.S. Pat. No. 7,364,858, EP 619 321, and EP 373 203, the entire teachings of which are incorporated by reference herein.

Susceptibility—In certain methods described herein, an individual who is at an increased susceptibility (i.e., increased risk) for any specific disease or trait under study (e.g., salt sensitivity of blood pressure or other conditions associated with paradoxical responses to salt intake), is an individual in whom at least one specific allele at one or more polymorphic marker or haplotype conferring (or is shown to correlate with) increased susceptibility for the disease or trait is identified (i.e., at-risk marker alleles or haplotypes). In one aspect, the at-risk marker or haplotype is one that confers a significant or substantial increased risk (or susceptibility) of the disease or trait. In one embodiment, susceptibility associated with a marker or haplotype is measured by a relative risk (RR). In another embodiment, susceptibility associated with a marker or haplotype is measured by an odds ratio (OR). In a further embodiment, the susceptibility is measured by a percentage. In one embodiment, an increased risk is measured as a risk (relative risk and/or odds ratio) of at least about 0.20, including but not limited to: at least about 0.25, at least about 0.30, at least about 0.5, at least about 0.75, at least about 1.00, at least about 1.05, at least about 1.10, at least about 1.11, at least about 1.12, at least about 1.13, at least about 1.14, at least about 1.15, at least about 1.16, at least about 1.17, at least about 1.18, at least about 1.19, or at least about 1.20 (e.g., at least about 1.3, at least about 1.4, at least about 1.5, at least about 1.6, at least about 1.7, at least about 1.8, at least about 1.9, at least about 2.0, at least about 2.5, at least about 3.0, at least about 4.0, and at least about 5.0). In a particular embodiment, a risk (relative risk and/or odds ratio) of at least 1.1 is deemed substantial. However, other cutoffs are also contemplated, e.g. at least 1.05, 1.15, 1.25, 1.35, and so on, and such cutoffs are also within scope of the invention. In other embodiments, a substantial increase in risk is at least about 5% or 10% or 15% or 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In one particular embodiment, a significant increase in risk is at least 10%. Other cutoffs or ranges as deemed suitable by the person skilled in the art to characterize the invention are however also contemplated, and those are also within scope of the invention.

An at-risk polymorphic marker or haplotype of the invention is one where at least one allele of at least one marker or haplotype is more frequently present in an individual at risk for the disease or trait (affected), or diagnosed with the disease or trait, compared to the frequency of its presence in a comparison group (control), such that the presence of the marker or haplotype is indicative of susceptibility to the disease or trait. The control group may in one embodiment be a population sample, i.e. a random sample from the general population. In another embodiment, the control group is represented by a group of individuals who are disease-free. Such a disease-free control may in one embodiment be characterized by the absence of one or more specific disease-associated symptoms (e.g., symptoms associated with salt sensitivity of blood pressure or other conditions associated with paradoxical responses to salt intake). In another embodiment, the disease-free control group is characterized by the absence of one or more disease-specific risk factors. Such risk factors included, but are not limited to, lifestyle, including but not limited to food and drink habits. In another embodiment, the risk factors are at least one genetic risk factor.

As an example of a simple test for correlation is a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes.

In other embodiments of the invention, an individual who is at a decreased susceptibility (i.e., at a decreased risk) for a disease or trait is an individual in whom at least one specific allele at one or more polymorphic marker or haplotype conferring decreased susceptibility for the disease or trait is identified. The marker alleles and/or haplotypes conferring decreased risk are also said to be protective. In one aspect, the protective marker or haplotype is one that confers a substantial decreased risk (or susceptibility) of the disease or trait. In one embodiment, substantial decreased risk is measured as a relative risk of less than 0.9, including but not limited to less than 0.9, less than 0.8, less than 0.7, less than 0.6, less than 0.5, less than 0.4, less than 0.3, less than 0.2 and less than 0.1. In one particular embodiment, substantial decreased risk is less than 0.7. In another embodiment, substantial decreased risk is less than 0.5. In yet another embodiment, substantial decreased risk is less than 0.3. In another embodiment, the decrease in risk (or susceptibility) is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 98%. In one particular embodiment, a substantial decrease in risk is at least about 30%. In another embodiment, a significant decrease in risk at least about 50%. In another embodiment, the decrease in risk is at least about 70%. Other cutoffs or ranges as deemed suitable by the person skilled in the art to characterize the invention are however also contemplated, and those are also within scope of the invention. For example, as shown herein multiple SNPs are associated with sensitivity to blood pressure and to paradoxical blood pressure responses to salt intake. Therefore, multiple markers may need to be taken into account in some embodiments.

An artisan of ordinary skill will appreciate that for markers with exactly two alleles present in the population being studied, and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

Treatment

The detection of the SNPs described herein for use in diagnosing salt sensitivity of blood pressure or paradoxical responses to salt intake can be further used to help establish a treatment regimen and for monitoring treatment. One of ordinary skill in the art will appreciate that a variety of drugs, or combinations of drugs, can be used based in the age, health, and other characteristics of the subject. A diet comprised of salt concentrations or amounts that do not exceed each subject's personal salt index can also be established to control sodium intake.

For example, a subject found to be sensitive can be treated with one or more diuretics, mineralocorticoid receptor antagonists, beta-blockers, alpha-blockers, ACE inhibitors, angiotensin II receptor blockers, calcium channel blockers, central agonists, peripheral-acting adrenergic blockers, direct vasodilators, or direct renin inhibitors. Use of these drugs can also be coupled with a diet to limit sodium intake.

The present invention further encompasses the use of drugs such as fenofibrate, which has been recently shown to lower blood pressure in salt-sensitive but not salt resistant hypertension (Gilbert et al., 2013, J. Hypertension).

The types of drugs, and some specific drugs, useful in the present invention include, but are not limited to:

Diuretics—
Some examples are:
Aldactone (spironolactone)
Dyrenium (triamterene)
Esidrix, Hydrodiuril, and Microzide (hydrochlorothiazide or HCTZ)
Hygroton and Thalitone (chlorthalidone)
Lasix (furosemide)
Lozol (indapamide)
Midamor (amiloride hydrochloride)
Mykrox and Zaroxolyn (metolazone)
Combination diuretics are also encompassed by the methods of the invention and include, but are not limited to:
Aldactazide (spironolactone and hydrochlorothiazide)
Dyazide and Maxzide (hydrochlorothiazide and triamterene)
Moduretic (amiloride hydrochloride and hydrochlorothiazide)
Beta-Blockers—
Examples of beta-blockers include, but are not limited to:
Blocadren (timolol)
Cartrol (carteolol hydrochloride)
Coreg (carvedilol)
Corgard (nadolol)
Inderal (propranolol)
Kerlone (betaxolol)
Levatol (penbutolol sulfate)
Lopressor and Toprol XL (metoprolol)
Sectral (acebutolol)
Tenormin (atenolol)
Visken (pindolol)
Zebeta (bisoprolol fumarate)

Normodyne and Trandate (labetolol)
Alpha-Blockers—
Examples of alpha-blockers, include, but are not limited to:
Cardura (doxazosin)
Hytrin (terazosin)
Minipress (prazosin)
ACE Inhibitors—
Angiotensin-converting enzyme inhibitors (ACE) are high blood pressure medications that prevent production of angiotensin II. Examples of ACE inhibitors include, but are not limited to:
Accupril (quinapril)
Altace (ramipril)
Capoten (captopril)
Mavik (trandolapril)
Lotensin (benazepril)
Monopril (fosinopril)
Prinivil and Zestril (lisinopril)
Univasc (moexipril)
Vasotec (enalapril)
ARBs (Angiotensin II Receptor Blockers)—
Examples of ARBs, include, but are not limited to:
Atacand (candesartan)
Avapro (irbesartan)
Benicar (olmesartan)
Cozaar (losartan)
Diovan (valsartan)
Micardis (telmisartan)
Teveten (eprosartan)
Calcium Channel Blockers (CCBs)—
Examples of CCBs include, but are not limited to:
Adalat and Procardia (nifedipine)
Calan, Covera, Isoptin, Verelan, and others (verapamil)
Cardene (nicardipine)
Cardizem, Cartia, Dilacor, and Tiazac (diltiazem)
DynaCirc (isradipine)
Norvasc (amlodipine)
Plendil (felodipine)
Sular (nisoldipine)
Central Agonists—
These medications target receptors. Examples of central agonists include, but are not limited to:
Aldomet (methyldopa)
Catapres (clonidine)
Tenex (guanfacine)
Wytensin (guanabenz)
Peripheral-Acting Adrenergic Blockers—
Examples of peripheral-acting adrenergic blockers include, but are not limited to:
Hylorel (guanadrel)
Ismelin (guanethidine)
Serpasil (reserpine)
Direct Vasodilators—
Examples of direct vasodilators:
Apresoline (hydralazine)
Loniten (minoxidil)
Direct Renin Inhibitors—
Direct renin inhibitors, ACE inhibitors, and ARBs all target the same process that narrows blood vessels. However, each type of medication blocks a different part of the process. Direct renin inhibitors block the enzyme renin from triggering a process that helps regulate blood pressure. Tekturna (aliskiren) is a direct renin inhibitor. Tekturna can be used alone or in combination with a diuretic or other medicines for high blood pressure.

The dosage of the active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present invention has application for both human and veterinary use.

For example, in one embodiment relating to oral administration to humans, a dosage of between approximately 0.1 and 300 mg/kg/day, or between approximately 0.5 and 50 mg/kg/day, or between approximately 1 and 10 mg/kg/day, is generally sufficient, but will vary depending on such things as the disorder being treated, the length of treatment, the age, sex, weight, and/or health of the subject, etc. The drugs can be administered in formulations that contain all drugs being used, or the drugs can be administered separately. In some cases, it is anticipated that multiple doses/times of administration will be required or useful. The present invention further provides for varying the length of time of treatment.

Methods for Predicting Response to Therapeutic Agents—

As is known in the art, individuals can have differential responses to a particular therapy (e.g., a therapeutic agent or therapeutic method). Pharmacogenomics addresses the issue of how genetic variations (e.g., the variants (markers and/or haplotypes) of the invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the invention), or therapeutic failure of the drug. Therefore, the variants of the invention may determine the manner in which a therapeutic agent and/or method acts on the body, or the way in which the body metabolizes the therapeutic agent.

Accordingly, in one embodiment, the presence of a particular allele at a polymorphic site or haplotype is indicative of a different response, e.g. a different response rate, to a particular treatment modality. This means that a patient diagnosed with salt sensitivity of blood pressure or other conditions associated with paradoxical responses to salt intake and carrying a certain allele at a polymorphic site or haplotype of the invention (e.g., the at-risk markers of the invention) would respond better to, or worse to, a specific therapeutic, drug and/or other therapy used to treat the disease. Therefore, the presence or absence of the marker allele or haplotype could aid in deciding what treatment should be used for the subject. For example, for a newly diagnosed patient, the presence of a marker or haplotype of the invention may be assessed (e.g., through testing DNA derived from a blood sample, as described herein). If the subject is positive for a marker allele or haplotype at (that is, at least one specific allele of the marker, or haplotype, is present), then the physician recommends one particular therapy, while if the patient is negative for the at least one allele of a marker, or a haplotype, then a different course of therapy may be recommended (which may include recommending that no immediate therapy, other than serial monitoring for progression of the disease, be performed). Thus, the patient's carrier status could be used to help determine whether a particular treatment modality should be administered. The value lies within the possibilities of being able to diagnose the disease at an early stage, to select the most appropriate treatment, and provide information to the clinician about prognosis/aggressiveness of the disease in order to be able to apply the most appropriate treatment.

Another aspect of the invention relates to methods of selecting individuals suitable for a particular treatment modality, based on the likelihood of developing particular complications or side effects of the particular treatment. It is well known that most therapeutic agents can lead to certain unwanted complications or side effects. Likewise, certain therapeutic procedures or operations may have complications associated with them. Complications or side effects of these particular treatments or associated with specific therapeutic agents can, just as diseases do, have a genetic component. It is therefore contemplated that selection of the appropriate treatment or therapeutic agent can in part be performed by determining the genotype of an individual, and using the genotype status of the individual to decide on a suitable therapeutic procedure or on a suitable therapeutic agent to treat the particular disease. It is therefore contemplated that the polymorphic markers of the invention can be used in this manner. In particular, the polymorphic markers of the invention can be used to determine whether administration of a particular therapeutic agent or treatment modality or method is suitable for the individual, based on estimating the likelihood that the individual will develop symptoms associated with salt sensitivity of blood pressure or other conditions associated with paradoxical responses to salt intake as a consequence of being administered the particular therapeutic agent or treatment modality or method. Indiscriminate use of such therapeutic agents or treatment modalities may lead to unnecessary and needless adverse complications.

The invention includes kits for assessing susceptibility of a subject to salt sensitivity of blood pressure or other condition disclosed herein. Each of the kits comprises reagents for selectively detecting at least one allele of at least one polymorphic marker of a group as described herein in the genome of the individual, and a collection of data comprising correlation data between the polymorphic markers and susceptibility to salt sensitivity of blood pressure or other condition disclosed herein.

EXAMPLES

Example 1

Methods
Study Participants
The present analyses were restricted to subjects with genotype and BP data: 55 hypertensive and 130 normotensive Caucasian subjects from the University of *Virginia* (UVA) discovery cohort and 211 Caucasian hypertensive subjects for the replication cohort (HyperPATH).
Human Subjects Protocol (UVA Cohort)
The study protocol and informed consent documents were approved by the University of Virginia Institutional Review Board for Health Sciences Research. Tests for genetic association for BP traits were performed in 185 subjects of European ancestry ages 18-70 years and body mass index (BMI) of 18-30. The subjects were deemed healthy as determined by screening history, physical examination, standard 12-lead electrocardiogram, and laboratory testing (complete blood count, fasting comprehensive metabolic panel, lipid panel and urinalysis with microscopy). The subjects were classified either as normotensive (NT; BP<140 SBP and <90 DBP mm Hg) or hypertensive (HT; history of prior diagnosis of hypertension or diastolic BP 90-114 mm Hg following a 3-week withdrawal from all antihypertensive medications or average BP readings during the pre-study screening period ≥140/90 mm Hg). Subjects with a history of malignant or accelerated hypertension, secondary causes of hypertension, contraindication to discontinuing antihypertensive medications, serum creatinine ≥1.5 mg/dL, urinary protein excretion >500 mg/day, continuing active urinary sediment, previous myocardial infarction, stroke or transient ischemic episode, congestive heart failure or severe small vessel disease or concurrent pregnancy were excluded. HT subjects with systolic BP>180 mm Hg or diastolic BP>114 mm Hg after withdrawal from antihypertensive medications also were excluded.

The study entailed 2 screening visits (genetic and pre-study) and a 3-week wash out period for HT subjects taking antihypertensive medications with weekly visits for BP monitoring. After completion of screening procedures and/or washout period, the subjects were placed on an isocaloric constant diet containing 1 g protein/kg body weight/day and 60 mmol/day of potassium ($K^+$) for 2 consecutive weeks. Individual caloric intake was determined by the subject's height, weight, and age and activity level. All food was weighed, measured, prepared, and obtained from the Research Diet Kitchen of the General Clinical Research Center of the University of Virginia Health System. On study days 1-7, $Na^+$ intake was either 10 mmol/day or 300 mmol/day and on study days 8-14 $Na^+$ intake was the opposite; the order of low and high $Na^+$ intake was randomized. BP, heart rate, height, and body weight were measured at each of 7 visits over the 2-week study period. BP measurements for the last day of each diet (3 separate measurements of BP taken over 45 minutes in the right arm with the subject in the sitting position) were averaged to identify salt sensitivity. Salt sensitivity was defined as a mean arterial pressure (MAP) increase of ≥7 mm Hg with the subject on high as compared with low $Na^+$ intake. $Na^+$ metabolic balance was confirmed with 3 consecutive 24-hr urine collections for $Na^+$ on the last 3 days of each diet. Subjects failing to achieve metabolic balance after a maximum of 7 days of the constant low or high $Na^+$ diet were excluded. HT subjects were excluded for systolic BP>180 mm Hg or diastolic BP>114 mm Hg or for persistent cardiovascular symptoms while on the diets. To assess whether or not the order of diets affected the diagnosis of salt sensitivity, we compared those receiving a high salt diet on the first week with those receiving a low salt diet on the first week. There was no evidence that the order of the diets affected the results (P=0.365, Wilcoxon Rank Sum test).
HyperPATH Cohort and Study Protocol
The HyperPATH Cohort consists of subjects with mild hypertension studied from four international centers [Brigham and Women's Hospital, University of Utah Medical Center, Vanderbilt University, and Hospital Broussais (Paris, France)]. The HyperPATH inclusion/exclusion criteria and the detailed phenotyping protocol have been previously described and are briefly detailed below. Although results from the HyperPATH have been reported previously, the present analyses are original.

All subjects received a screening history, and physical and laboratory examinations. Hypertension was defined as a seated diastolic BP of ≥100 mmHg off antihypertensive medications, ≥90 mmHg while taking ≥1 medication, or treatment with ≥2 medications. Subjects requiring ≥4 antihypertensive medications were excluded. A diagnosis of diabetes mellitus (previously diagnosed, fasting glucose >126 mg/dl, or glucose >200 mg/dl at 180 minutes after 75 gm glucose load), overt renal insufficiency (serum creatinine>1.5 mg/dL), stroke, psychiatric illness, any form of secondary hypertension, obesity (BMI>30 kg/m$^2$), current tobacco, or illicit drug use were excluded. Subjects with abnormal laboratory values or electrocardiographic evidence of heart block, ischemia, or prior coronary events at screening were excluded. All subjects were between the ages of 18-65 years. Race was self-defined by each subject.

To control for the influence that medications may play on the renin-angiotensin-aldosterone system, all angiotensin converting enzyme inhibitors (ACEI), angiotensin receptor blockers (ARB), or mineralocorticoid receptor antagonists were discontinued 3 months and β-adrenergic receptor blockers were discontinued 1 month prior to the start of the study. If necessary, subjects were placed on amlodipine or hydrochlorothiazide for BP control. All medications were discontinued 2 weeks prior to the start of the study.

All participants received two alcohol and caffeine free isocaloric diets for 5-7 days each on an outpatient basis: high sodium (HS) (200 mmol/day) and low sodium (LS) (10 mmol/day) with each diet also containing 100 mmol/day potassium and 20 mmol/day calcium. Subjects were then admitted overnight to the in-patient research center (PRC) after each diet. On the final day of each diet, a 24-hour urine collection was obtained. All studied participants had a urine sodium ≥150 mmol/24 hours on the HS diet and ≤30 mmol/24 hours on the LS diet. BP measurements were obtained using an automated device (DINAMAP; Critikon, Tampa, Fla.). Three consecutive readings separated by 5 minutes were obtained after each diet and measured while the subject was supine. Salt sensitivity was defined as a mean arterial pressure (MAP) increase of ≥7 mm Hg with the subjects on high as compared with low Na$^+$ intake.

Candidate Gene and SNP Selection and Genotyping

Candidate SNPs were selected based on prior association with salt sensitivity or hypertension. In the UVA cohort, each SNP was genotyped using a fluorescent allele-specific PCR (AS-PCR) based assay. This method has also been referred to in the literature as PCR amplification of specific alleles (PASA). Reaction components were assembled on a 384-well array tape platform (See Douglas Scientific's website) using nanoliter volumes (500-1000 nl). PCR was carried out in a water bath thermocycler using standard 3-stage parameters (denature, primer annealing, primer extension). The specific parameters of each PCR varied depending on the nature of the primers and the SNP being genotyped. The 384 well array tape was scanned after PCR amplification and the ratio of fluorescent signals was used to determine the genotype (homozygous for one allele or heterozygous).

In the HyperPATH cohort two SNPs in the SLC4A5 gene were genotyped for replication purposes: rs7571842 and rs10177833. The SNPs were genotyped using a 7600-SNP Illumina iSelect platform (Illumina, San Diego, Calif.). These genotyped SNPs had a completion rate of greater than 90% and were in Hardy-Weinberg equilibrium (HWE). Repeat genotyping demonstrated concordance with the original genotype call.

Statistical Analysis

Statistical analyses related to the UVA cohort were performed using STATA (Version 11). Genotypic association was assessed for hypertension status at baseline and salt sensitivity (defined as ≥7 mmHg increase in MAP on a high salt diet) using Chi squared or Fisher's Exact test, where appropriate. For SNPs that showed suggestive evidence of association (P≤0.1) logistic regression analyses were performed without adjustments for covariates and then adjusted for body mass index (BMI), age, and gender for the hypertension comparison and for BMI and age for salt sensitivity analyses. All SNPs were tested for HWE in cases and controls separately. Results were not adjusted for multiple comparisons; instead significant results were tested for replication to assess for false positives in the HyperPATH data.

Statistical analyses related to the HyperPATH cohort were performed using SAS 9.1 (SAS Institute). HWE was evaluated using a chi-square test. Population characteristics are displayed as mean values with standard deviations. Non-normally distributed variables are shown as median values with the inter-quartile range. Logistic regression analyses were performed for salt sensitivity analyses and adjusted for age, BMI, sibling relatedness, and study site. A dominant genetic model (major allele homozygotes versus heterozygotes plus minor allele homozygotes) was conducted for all analyses.

Meta-Analysis

Genetic meta-analysis was conducted using a weighted Z-score method and implemented in the freely available METAL software package (available online at the University of Michigan Center for Statistical Genetics website). This approach accounts for the direction of association relative to a chosen reference allele and the sample size of each cohort. First, P values from each study are converted to Z scores. A weighted sum of Z scores is calculated where each statistic is weighted by the square root of the sample size for each study. The resulting sum is divided by the square root of the total sample size to obtain an overall Z statistic Results Characteristics of the Discovery (UVA) Study Subjects General Characteristics.

Tests for genetic association for BP traits were performed in 185 UVA subjects. Of the 185 UVA subjects, 55 were HT at the initiation of the study. The HT group was heavier, older and had a larger proportion of males than the NT subjects (P≤0.0007 for all comparisons; Table 1A and 1B). There were 34 subjects in the SS group and 151 subjects in the salt-resistant (SR) group (Table 1B). The SS subjects were older than the SR subjects. There was no significant difference in BMI between SS and SR subjects. As expected, the distribution of SS subjects differed between the HT and NT subjects (P=0.004; Table 1C). Demographic and clinical descriptions of the HyperPATH data are presented in Table S1.

High Na$^+$ Intake.

After 7 days of high Na$^+$ intake, urinary Na$^+$ excretion was similar in the UVA SS and SR groups at 226.3±37.8 and 218.8±57.3 mmol/24 hr, respectively (P=0.52). With subjects on high Na$^+$ intake, systolic, diastolic and mean arterial pressures were higher in the SS than the SR group (all P<0.0001). There were no differences in resting heart rate, plasma renin activity, or urine creatinine excretion between the SS and SR groups for either population.

Low Na$^+$ Intake.

Following 7 days of low Na$^+$ intake, urinary Na$^+$ excretion also was similar in the SS and SR groups at 18.6±6.2 and 17.4±7.4 mmol/24 hr, respectively (P=0.31). With subjects on low Na$^+$ intake, diastolic BP was higher in the SR group (P=0.02), but there was no significant difference in systolic or mean arterial pressure between the two groups. There were no differences in resting heart rate or total urine creatinine excretion between the SS and SR groups. However, on high Na$^+$ intake plasma renin activity was higher in the SR subjects (P=0.03). The mean change in blood pressure from high salt to low salt diet did not differ from that of low salt to high salt diet (P=0.365).

Effect of High and Low Na$^+$ Intake on BP, Plasma Renin Activity and Plasma Aldosterone Concentrations.

For both SS and SR groups, urinary Na$^+$ excretion was more than 10-fold higher with subjects on high as opposed to low Na$^+$ intake (P<0.0001 for both groups). In the SS group, systolic, diastolic, and mean arterial pressures were higher during high as compared with low Na$^+$ intake (all P<0.0001). However, for the SR group BP was not influenced by Na$^+$ intake. Plasma renin activity and aldosterone concentrations were both higher with low than high Na$^+$ intake (P<0.0001).

Genetic Association Studies

A total of 35 SNPs in 17 candidate genes were assayed in the UVA population, but of these eight were monomorphic in one phenotypic class and/or near monomorphic in the other, and therefore not presented. (Table 2; Tables S2 and S3; please see Online Data Supplement at the American Heart Association Journals website and in the appendix). Association analyses with salt sensitivity demonstrated four variants that were marginally associated with salt sensitivity, the two SNPs in SLC4A5, one SNP in the dopamine D$_2$ receptor (DRD2, rs6276) and one SNP in G protein-coupled receptor kinase-4 (GRK4, rs2960306) (P<0.1; Table 2). Association with hypertension at baseline revealed two SNPs with a P value below 0.10: rs4691 in ADD1 (P=0.0276) and rs1801058 in GRK4 (P=0.018).

Each of these SNPs was examined for association using logistic regression to determine effect sizes, and to assess whether or not adjusting for covariates affected the results. For salt sensitivity only the two SNPs in SLC4A5 (rs7571842 and rs10177833) demonstrated significant results using logistic regression. These two SNPs had P values of $1.04 \times 10^{-4}$ and $3.1 \times 10^{-4}$ and odds ratios (OR) of 0.221 and 0.221, respectively (Table 3A). After adjusting for BMI and age, the associations remained (P=$8.9 \times 10^{-5}$ and $2.55 \times 10^{-4}$ and odds ratios (OR) 0.310 and 0.286, respectively). These two SLC4A5 SNPs were in linkage disequilibrium in both SS and SR UVA subjects, but the strength of the linkage disequilibrium was greater in SR than SS subjects ($r^2$=0.93 and 0.61 respectively), further supporting the conclusion of an association of SLC4A5 with SS. The DRD2 SNP was still close to significant after adjusting for covariates (P=0.052). For the hypertension analysis, the associations between GRK4 rs1801058 and ADD1 rs4961 remained significant (P<0.05) after adjusting for covariates (Table 3B)

Because ADD1 and GRK4 are within 40 kb of each other, we adjusted each the logistic regression analyses for the other SNPs in addition to gender, BMI, and age to assess independence of these two SNPs. After adjustment for rs4961, rs1801058 remained statistically significant (p=0.016, OR 0.545, 0.330-0.891 95% CI), but the ADD1 SNP rs4961 did not remain significant after adjusting for GRK4 genotypes (p=0.524, OR 0.968, 0.877-1.07 95%, CI).

Replication of the Association of SLC4A5 SNPs and Salt Sensitivity of BP: HyperPATH Protocol Replication Associations between the two SLC4A5 SNPs from the UVA cohort and salt sensitivity were also tested in the HyperPATH cohort (Table 3A) and significant associations were found for rs7571842 (P=0.02). SNP rs1017783 manifested trends for salt sensitivity that did not reach statistical significance (Table 3A, P=0.06). The effects were in the same direction as for the UVA analyses.

Meta-Analysis

A meta-analysis of the two cohorts was carried out for salt sensitivity. As expected, both SNPs demonstrated highly significant associations with increased salt sensitivity (Table 4) [rs7571842 (P=$1.2 \times 10^{-5}$), rs1017783 (P=$1.1 \times 10^{-4}$)].

Example 2—Increased BP on a Low Salt Diet—DRD2 SNP Rs6276

A small group of subjects were found to have an increase in BP on a low salt diet. When tested for associations, it was found unexpectedly that a SNP in the dopamine type 2 receptor—rs6276 (DRD2) showed a positive association: Odds Ratio (OR) of 2.6 and a p value ~0.0008 in an adjusted model. DRD2 is on 11q22-q23. The NCBI Ref. Seq. No. is NC_000011.9 and it is 85,433 bp DNA.

There is currently no diagnostic test for these individuals who have a paradoxical increase in blood pressure on a low salt diet. The present invention therefore encompasses such a diagnostic test.

Example 3—Negative Response to Salt Loading—DRD2 SNP Rs6276

Lastly, it was determined whether there were any associations with a negative response to salt loading (i.e., a decrease of MAP with high sodium intake), using the subjects of Table 1B.

Unexpectedly, one SNP in DRD2 (rs6276) revealed a highly significant negative association (P<0.0009, odds ratio=2.6 (unadjusted) or P<0.0007, odds ratio=2.6 (adjusted).

This demonstrates that rs6276 is negatively associated with salt sensitivity of blood pressure. No diagnostic currently exists for this relationship.

Therefore, SLC4A5 variants are strongly associated with salt sensitivity and DRD2 is negatively associated with salt sensitivity in Caucasians.

Discussion

Despite numerous genome-wide association studies (GWAS), the specific genetic causes of hypertension and/or salt sensitivity of BP have remained elusive. Several genes identified from GWAS have been shown collectively only to influence 2% of BP variability. It is likely that the lack of variance is because GWAS was not designed to account for epistatic or gene-environment interactions. Salt sensitivity is of particular interest since the prevalence is estimated to be as high as 73% in hypertensive and 36% in normotensive Blacks. In Koreans, the incidence of salt sensitivity is 28%. Retrospective studies have demonstrated that normotensives with salt sensitivity have mortality estimates that are equivalent to those of hypertensive subjects. Thus, the identification of gene variants associated with salt sensitivity might provide predictive testing to identify subjects for further workup and/or treatment.

Various DNA polymorphisms have been associated with salt sensitivity of BP. In Koreans, 4 gene variants were strongly associated with salt sensitivity: cytosolic branched chain aminotransferase 1 (BCAT1, rs7961152, odds ratio=4.9, P=0.007); ATPase, Ca$^{++}$ transporting, plasma membrane 1 (ATP2B1, rs2681472, odds ratio=3.8, P=0.040); fibroblast growth factor 5 (FGF5, rs16998073, odds ratio=2.1, P=0.042); and LOC100132798 (rs2398162; odds ratio=3.5, P=0.023). In elderly Amish, the Ste29-related proline-alanine-rich kinase (SPAK) protein contains two polymorphisms in the STK39 locus (rs3754777 and rs6749447) that are associated with salt sensitivity. We previously demonstrated that SNPs in GRK4 are highly associated with salt-sensitive hypertension in Japanese and Italians which was recapitulated in transgenic mice expressing the human GRK4 variants. Additional polymorphisms in α-adducin (ADD1), angiotensin converting enzyme (ACE), angiotensinogen (AGT), cytochrome P450/11B polypeptide 2 (CYP11B2), G-protein β3 subunit (GNβ3), and neural precursor cell expressed developmentally down-regulated 4-like protein (NEDD4L) have been linked to salt-sensitive hypertension. Since it is of interest to determine if candidate genes are associated with salt sensitivity, independently of hypertension, we examined polymorphisms in a Caucasian cohort, containing subjects who were both NT and HT that had been phenotyped for salt sensitivity using controlled diets. Of importance most of the variants studied were non-synonymous coding variants or those already shown to have biological function. Our results demonstrate that SLC4A5 variants are strongly associated with salt sensitivity in Caucasians.

SLC4A5 was originally cloned from human heart in 2000. Chromosome 2, the location of SLC4A5, was linked to increased BP in Blacks and Caucasians. Building on this evidence, SLC4A5 was identified as a candidate hypertension susceptibility gene using several combined positional candidate gene methods. Selected single nucleotide polymorphisms at positions SLC4A5 (rs6731545), SLC4A5 A/C (rs1017783) and SLC4A5 A/G (rs7571842) were associated with elevated heart rate and BP in both Caucasians and African-American. Our results are consistent in that the allele associated with increased BP in Hunt et al. was also our risk allele (A) for salt sensitivity of BP.

The SLC4A5 gene codes for Na$^+$-bicarbonate co-transporter-4 (NBC4), also termed NBCe2, an electrogenic Na$^+$-bicarbonate co-transporter that helps maintain the homeostasis of intracellular pH by co-transporting three bicarbonate anions for each Na$^+$ cation independently of chloride. Not much is known about the role of NBCe2 in renal physiology. NBCe2 is expressed in various organs including the kidney, heart, brain. Within the human kidney, NBCe2 mRNA is expressed in the thick ascending limb of Henle and the protein has been localized in the luminal plasma membranes of the cortical collecting duct. A recent study demonstrated that SLC4A5 knockout mice are hypertensive and have compensated metabolic acidosis. It was reasoned that deletion of SLC4A5 initiates compensatory bicarbonate reabsorption via other Nat bicarbonate transporters at the expense of increased tubule Na$^+$ uptake. Investigators also have speculated that NBCe2 might be a promising candidate for the strong linkage signal found in response to renin-angiotensin system inhibiting drugs, highlighting its potential importance in SS hypertension Our results provide a new line of strong evidence that this gene is associated with BP phenotypes in general and salt sensitivity of BP in particular.

Strengths of the analysis include (1) use of extensive phenotyping including dietary control of Na$^+$, (2) use of a meta-analysis approach to validate prior findings and (3) the fact that similar results were found in two independent studies.

TABLE 1

Characteristics of the Discovery Study Population[1]

A. Hypertension Status of UVA Study Subjects (Mean ± SD)

| Pre-study screen | Hypertensive group | Normotensive group | P value |
| --- | --- | --- | --- |
| Number of subjects | 55 | 130 | |
| Male | 29 | 43 | 0.004 |

TABLE 1-continued

Characteristics of the Discovery Study Population[1]

| | | | |
| --- | --- | --- | --- |
| Female | 26 | 87 | |
| Age (yrs) | 52.4 ± 12.3 | 45.0 ± 13.9 | 0.0007 |
| BMI | 25.8 ± 2.9 | 24.1 ± 2.9 | 0.0004 |
| Systolic BP (mmHg) | 136 ± 11.5 | 118.9 ± 11.6 | <0.0001 |
| Diastolic BP (mmHg) | 80.5 ± 9.1 | 71.5 ± 7.1 | <0.0001 |
| MAP (mmHg) | 99.0 ± 9.2 | 87.3 ± 7.9 | <0.0001 |

1B. Salt sensitivity Status of UVA Study Subjects (Mean ± SD):

| Pre-study (Visit 1 or pre-study screen) | Salt-Sensitive Subjects | Salt-Resistant Subjects | P value |
| --- | --- | --- | --- |
| Number of subjects | 34 | 151 | |
| Male | 10 | 62 | 0.208[2] |
| Female | 24 | 89 | |
| Age (yrs) | 52.3 ± 13.9 | 46.0 ± 13.6 | 0.0156 |
| BMI | 25.4 ± 2.7 | 24.4 ± 3.0 | 0.0740 |
| After High Salt diet | | | |
| Systolic (mmHg) | 133.5 ± 11.6 | 120.1 ± 13.2 | <0.0001 |
| Diastolic (mmHg) | 79.4 ± 7.6 | 71.7 ± 8.9 | <0.0001 |
| MAP (mmHg) | 97.4 ± 7.5 | 87.8 ± 9.7 | <0.0001 |
| Heart Rate (Beats/min) | 65.8 ± 9.3 | 68.8 ± 11.1 | 0.1552 |
| Plasma Renin Activity (ng/mL/hr) | 0.39 ± 0.20 | 0.58 ± 0.49 | 0.0352 |
| Plasma Aldosterone (ng/dL) | 4.02 ± 2.85 | 3.65 ± 3.29 | 0.5520 |
| Urinary Sodium Excretion (mmol/24 hrs) | 226.3 ± 37.8 | 218.8 ± 57.3 | 0.5186 |
| Total Urine Creatinine (g/24 hrs) | 1.31 ± 0.4 | 1.31 ± 0.4 | 0.4576 |
| After Low Salt diet | | | |
| Systolic (mmHg) | 118.6 ± 11.5 | 119.2 ± 15.4 | 0.8510 |
| Diastolic (mmHg) | 70.3 ± 5.2 | 74.1 ± 9.0 | 0.0192 |
| MAP (mmHg) | 86.4 ± 6.4 | 89.1 ± 9.5 | 0.1078 |
| Heart Rate (Beats/min) | 72.5 ± 9.0 | 74.1 ± 10.9 | 0.4100 |
| Plasma Renin Activity (ng/mL/hr) | 4.5 ± 3.4 | 6.1 ± 3.7 | 0.0303 |
| Plasma Aldosterone (ng/dL) | 27.9 ± 12.8 | 34.1 ± 19.8 | 0.0830 |
| Urinary Sodium Excretion (mmol/24 hrs) | 18.6 ± 6.2 | 17.4 ± 7.4 | 0.3076 |
| Total Urine Creatinine (g/24 hrs) | 1.3 ± 0.3 | 1.3 ± 0.4 | 0.6872 |

1C. Distribution of Salt sensitivity Status between UVA Hypertensive and Normotensive Study Subjects

| BP status | SS (Case) | SR (Control) | Total |
| --- | --- | --- | --- |
| HTN | 17(50%, 30.9%) | 38(25.2%, 69.1%) | 55 |
| NTN | 17(50%, 13.1%) | 113(74.8%, 86.9%) | 130 |
| Total | 34 | 151 | 185 (100%) |

If continuous variables were normally distributed, a t-test was used to compare the two groups. If not normally distributed, a Wilcoxon-Rank Sum was used to compare the two groups. The non-normal variables were age, MAP (low salt), systolic (low salt), and diastolic (high and low salt[2] Comparison of distribution of gender in SS vs. SR subjects

TABLE 2

Associations of Candidate Gene SNPs with Salt sensitivity and Blood Pressure

| Gene Name | Gene Designation | SNP Designation | rs number | SS Status vs Genotype P value[1] | HTN Status vs Genotype P value[1] |
|---|---|---|---|---|---|
| Aldosterone synthase | CYP11B2 | C-344T, 5' near gene | rs1799998 | 0.8504 | 0.331 |
| Alpha Adducin 1 | ADD1 | G460W | rs4961 | 0.443[2] | 0.027[2] |
| Alpha Adducin 2 | ADD2 | Intron 2 | rs1541582 | 0.194[2] | 0.897[2] |
| Angiotensinogen | AGT | M268T | rs699 | 0.326 | 0.885 |
| Angiotensin II Receptor, Type I | AGTR1 | A1166C, 3' UTR | rs5186 | 0.936[2] | 0.135 |
| Angiotensin Converting Enzyme | ACE | Intron 15 | rs1799752 | 0.610 | 0.228 |
| Caveolin 1 | CAV1 | Intron 2 | rs3807990 | 0.576 | 0.767[2] |
|  |  | Intron 2 | rs3840634 | 0.813[2] | 0.271[2] |
| Cholecystokinin A Receptor | CCKAR | H210Y | rs41267457 | NA | NA |
| Cholecystokinin B Receptor | CCKBR | L37F | rs1805000 | NA | NA |
|  |  | V125I | rs1805002 | 0.247[2] | 0.908 |
| Cytochrome P450-4A11 | CYP4A11 | F434S | rs1126742 | 0.623[2] | 0.334[2] |
| Dopamine Receptor D2 | DRD2 | −141C, 5' near gene | rs1799732 | 0.574[2] | 0.374[2] |
|  |  | E713K | rs1800497 | 0.721[2] | 0.603[2] |
|  |  | Intron 1 | rs1079597 | 0.721[2] | 0.302[2] |
|  |  | 3' UTR | rs6276 | 0.074[2] | 0.584[2] |
| G Protein-coupled Receptor Kinase 4 | GRK4 | R65L | rs2960306 | 0.020 | 0.227 |
|  |  | A142V | rs1024323 | 0.389 | 0.500 |
|  |  | A486V | rs1801058 | 0.846 | 0.018 |
| Nitric Oxide Synthase 3 (endothelial cell) | eNOS | E298D | rs1799983 | 0.170 | 0.376 |
| Protein Phosphatase 2, Regulatory Subunit B, Gamma Isoform | PPP2R2C | T146T | rs35368770 | NA | NA |
|  |  | T204T | rs35410672 | NA | NA |
|  |  | I429I | rs3796403 | 0.892 | 0.281 |
|  |  | A431A | rs11545013 | NA | NA |
| Sodium Bicarbonate Cotransporter, Member 5 | SLC4A5 | Intron 17 | rs7571842 | <0.001[2] | 0.825 |
|  |  | Intron 20 | rs10177833 | <0.001[2] | 0.849 |
| Sorting Nexin 1 | SNX1 | E33R, frameshift | rs34910981 | NA | NA |
|  |  | P211S | rs1130604 | NA | NA |
|  |  | D466N | rs1802376 | NA | NA |
| Sorting Nexin 5 | SNX5 | P92L | rs6045116 | NA | NA |
| Sorting Nexin 19 | SNX19 | V361L | rs3751037 | 0.198[2] | 0.231[2] |
|  |  | S407G | rs3190345 | 0.319 | 0.434[2] |
|  |  | L618F | rs681982 | NA | NA |
|  |  | N753S | rs4414223 | 0.230[2] | 0.185[2] |
|  |  | L878R | rs2298566 | 0.361 | 0.320[2] |

[1]P values based on 2 × 3 Chi square analyses unless otherwise noted.
[2]Based on pooling rare homozygotes with heterozygotes due to there being too few homozygotes.
NA—Not analyzed because minor allele frequency is too low

TABLE 3

Logistic Regression Analyses for Both Cohorts

| Gene | SNP | Referent Allele | OR unadjusted | 95% CI | P value | OR adjusted for BMI and age | 95% CI | P value |
|---|---|---|---|---|---|---|---|---|
| A. Logistic Regression Analyses for Salt sensitivity | | | | | | | | |
| DRD2 | rs6276 | A | 2.3 | 0.991-5.340 | 0.053 | 2.316 | 0.994-5.394 | 0.052 |
| GRK4 | rs2960306 | G | 1.098 | 0.656-1.838 | 0.721 | 1.096 | 0.652-1.842 | 0.730 |
| SLC4A5UVA | rs7571842 | A | 0.221 | 0.155-0.576 | 0.000104 | 0.210 | 0.0962-0.458 | 0.0000894 |
| SLC4A5 HyperPATH | Rs7571842 | A |  |  |  | 0.32 | 0.21-0.47 | 0.02 |
| SLC4A5UVA | rs1017783 | A | 0.221 | 0.103-0.473 | 0.000310 | 0.286 | 0.146-0.559 | 0.000255 |
| SLC4A5 HyperPATH | rs1017783 | A |  |  |  | 0.36 | 0.23-0.51 | 0.06 |

TABLE 3-continued

Logistic Regression Analyses for Both Cohorts

3B. Logistic Regression Analyses for Hypertension

| Gene | SNP | Referent Allele | OR unadjusted | 95% CI | P value | OR adjusted for gender, BMI, and age | 95% CI | P value |
|---|---|---|---|---|---|---|---|---|
| GRK4 | rs1801058 | C | 0.607 | 0.385-0.957 | 0.032 | 0.544 | 0.335-0.883 | 0.014 |
| ADD1 | rs4961 | G | 0.422 | 0.208-0.855 | 0.017 | 0.406 | 0.191-0.861 | 0.019 |

TABLE 4

Meta-Analysis for SNP-Salt-Sensitive Blood Pressure Association

| | SNP | N | Single Association P-value | Meta P-value |
|---|---|---|---|---|
| UVA | rs7571842 | 185 | 0.000104 | $1.2 \times 10^{-5}$ |
| HyperPATH | rs7571842 | 211 | 0.02 | |
| UVA | rs1017783 | 185 | 0.000310 | $1.1 \times 10^{-4}$ |
| HyperPATH | rs1017783 | 211 | 0.06 | |

The P-value for the association of both SNPs with salt sensitive blood pressure accounts for age and BMI.
UVA = University of Virginia, SNP = single nucleotide polymorphism, BMI = body mass index.

TABLE S1

HyperPATH Demographic and Clinical Data

A. HyperPATH Demographic Data

| Pre-Study Screen | HTN |
|---|---|
| Number of subjects | 211 |
| Male | 129 |
| Female | 82 |
| Age (yrs) | 49.2 ± 8.4 |
| BMI | 26.1 ± 2.4 |
| Systolic BP (mmHg) | 147.5 ± 19.1 |
| Diastolic BP (mmHg) | 88.8 ± 12.1 |
| MAP (mmHg) | 105.8 ± 13.4 |

B. HyperPATH Salt sensitivity Data

| Baseline | Salt-Sensitive Subjects | Salt-Resistant Subjects |
|---|---|---|
| Number of subjects | 140 | 71 |
| Male | 89 | 40 |
| Female | 51 | 31 |
| Age (yrs) | 49.8 ± 8.4 | 48.1 ± 8.4 |
| BMI | 26.1 ± 2.4 | 26.1 ± 2.6 |
| After High Salt diet | | |
| Systolic (mmHg) | 151.05 ± 17.4 | 140.4 ± 20.4 |
| Diastolic (mmHg) | 91.9 ± 10.3 | 82.6 ± 12.9 |
| MAP (mmHg) | 109.0 ± 11.2 | 96.7 ± 15.3 |
| Heart Rate (Beats/min) | 63.2 ± 10.0 | 64.1 ± 9.9 |
| Plasma Renin Activity (ng/mL/hr) | 0.55 ± 0.52 | 0.88 ± 1.6 |
| Plasma Aldosterone (ng/dL) | 5.4 ± 3.7 | 5.6 ± 3.7 |
| Urinary Sodium Excretion (mmol/24 hrs) | 228.6 ± 69.2 | 218.3 ± 69.3 |
| Total Urine Creatinine (g/24 hrs) | 1.43 ± 0.4 | 1.44 ± 0.4 |
| After Low Salt diet | | |
| Systolic (mmHg) | 128.4 ± 14.9 | 137.8 ± 19.2 |
| Diastolic (mmHg) | 78.1 ± 10.8 | 82.4 ± 11.9 |
| MAP (mmHg) | 94.5 ± 11.6 | 95.7 ± 15.6 |
| Heart Rate (Beats/min) | 64.5 ± 10.1 | 64.8 ± 8.9 |
| Plasma Renin Activity (ng/mL/hr) | 3.1 ± 8.0 | 2.7 ± 1.8 |
| Plasma Aldosterone (ng/dL) | 17.4 ± 10.5 | 18.4 ± 17.0 |
| Urinary Sodium Excretion (mmol/24 hrs) | 13.5 ± 7.9 | 13.4 ± 8.4 |

TABLE S2

Distribution of Genotypes in Hypertensive and Normotensive Subjects in the UVA Cohort

| Gene | SNP | | Genotypes | | | MAF | HWE |
|---|---|---|---|---|---|---|---|
| CYP11β2 | rs1799998 | | CC | CT | TT | | |
| | | HT | 6 | 24 | 15 | 0.4000 | 0.6473 |
| | | NT | 26 | 57 | 29 | 0.4866 | 0.8645 |
| ADD | rs4961 | | GG | GT | TT | | |
| | | HT | 34 | 12 | 0 | 0.1304 | 0.2560 |
| | | NT | 61 | 44 | 6 | 0.2523 | 1.000 |
| | rs1541582 | | AA | AT | TT | | |
| | | HT | 26 | 14 | 4 | 0.2500 | 1.000 |
| | | NT | 62 | 41 | 4 | 0.2290 | 1.000 |
| AGT | rs699 | | CC | TC | TT | | |
| | | HT | 8 | 20 | 19 | 0.3830 | 0.2042 |
| | | NT | 20 | 43 | 49 | 0.8850 | 0.1429 |
| AGTR1 | rs5186 | | AA | CA | CC | | |
| | | HT | 12 | 27 | 5 | 0.4205 | 1.000 |
| | | NT | 49 | 50 | 12 | 0.3333 | 0.4496 |
| ACE | rs1799752 | | long long | long short | short short | | |
| | | HT | 5 | 31 | 10 | 0.4457 | 0.619 |
| | | NT | 20 | 59 | 33 | 0.4420 | 0.06182 |
| CAV | rs3807990 | | CC | CT | TT | | |
| | | HT | 25 | 17 | 2 | 0.2386 | 1.000 |
| | | NT | 63 | 37 | 6 | 0.2311 | 07967 |
| | rs3840634 | | Del Del | Ins Del | Ins Ins | | |
| | | HT | 2 | 17 | 24 | 0.2442 | 0.3710 |
| | | NT | 2 | 35 | 70 | 0.1822 | 0.2821 |
| CCKAR | rs41267457 | | GG | GA | AA | | |
| | | HT | 46 | 1 | 0 | 0.0213 | 1.000 |
| | | NT | 112 | 2 | 0 | 0.0175 | 1.000 |
| CCKBR | rs1805000 | | CC | CT | TT | | |
| | | HT | 44 | 2 | 0 | 0.0217 | 1.000 |
| | | NT | 110 | 0 | 1 | 0.0090 | 0.01099 |
| | rs1805002 | | GG | GA | AA | | |
| | | HT | 43 | 4 | 0 | 0.0851 | 1.000 |
| | | NT | 104 | 9 | 0 | 0.0398 | 1.000 |
| CYP4A11 | rs1126742 | | TT | CT | CC | | |
| | | HT | 34 | 9 | 2 | 0.1444 | 1.000 |
| | | NT | 76 | 35 | 2 | 0.1726 | 1.000 |
| DRD2 | rs1799732 | | Del Del | Ins Del | Ins Ins | | |

TABLE S2-continued

Distribution of Genotypes in Hypertensive and Normotensive Subjects in the UVA Cohort

| Gene | SNP | | Genotypes | | MAF | HWE |
|---|---|---|---|---|---|---|
| | | HT | 1 | 8 | 37 | 0.1087 | 0.1518 |
| | | NT | 0 | 15 | 93 | 0.0694 | 1.000 |
| | rs1800497 | | CC | TC | TT | | |
| | | HT | 28 | 16 | 2 | 0.2174 | 1.000 |
| | | NT | 62 | 40 | 8 | 0.2545 | 0.8254 |
| | rs1079597 | | AA | GA | GG | | |
| | | HT | 1 | 13 | 33 | 0.1596 | 1.000 |
| | | NT | 6 | 37 | 69 | 0.2188 | 0.8025 |
| | rs6276 | | AA | AG | GG | | |
| | | HT | 25 | 17 | 4 | 0.2717 | 1.000 |
| | | NT | 54 | 45 | 10 | 0.2982 | 0.5367 |
| GRK4 | rs2960306 | | GG | GT | TT | | |
| | | HT | 26 | 19 | 10 | 0.3545 | 0.5394 |
| | | NT | 46 | 62 | 22 | 0.227 | 0.2571 |
| | rs1024323 | | CC | CT | TT | | |
| | | HT | 24 | 22 | 9 | 0.3636 | 0.2889 |
| | | NT | 45 | 62 | 23 | 0.4154 | 0.4196 |
| | rs1801058 | | CC | CT | TT | | |
| | | HT | 26 | 19 | 10 | 0.3545 | 0.6353 |
| | | NT | 34 | 67 | 29 | 0.4808 | 0.6361 |
| eNOS | rs1799983 | | GG | TG | TT | | |
| | | HT | 22 | 17 | 5 | 0.3068 | 0.6478 |
| | | NT | 46 | 55 | 8 | 0.3257 | 0.2353 |
| PPP2R2C | rs35368770 | | GG | GA | AA | | |
| | | HT | 46 | 1 | 0 | 0.0213 | 1.000 |
| | | NT | 109 | 1 | 0 | 0.0091 | 1.000 |
| | rs35410672 | | CC | CT | TT | | |
| | | HT | 46 | 0 | 0 | 0 | 1.000 |
| | | NT | 111 | 2 | 0 | 0.0177 | 1.000 |
| | rs3796403 | | AA | GA | GG | | |
| | | HT | 10 | 29 | 6 | 0.4556 | 0.3556 |
| | | NT | 37 | 56 | 17 | 0.4091 | 0.2939 |
| | rs11545013 | | CC | AC | AA | | |
| | | HT | 47 | 0 | 0 | 0 | 1.000 |
| | | NT | 110 | 1 | 0 | 0.0090 | 0.1418 |
| SLC4A5 | rs7571842 | | AA | GA | GG | | |
| | | HT | 14 | 21 | 12 | 0.4787 | 1.000 |
| | | NT | 34 | 55 | 24 | 0.4558 | 0.4952 |
| | rs10177833 | | AA | AC | CC | | |
| | | HT | 12 | 21 | 9 | 0.5357 | 0.3428 |
| | | NT | 34 | 55 | 19 | 0.4306 | 1.000 |
| SNX1 | rs1130604 | | CC | TC | TT | | |
| | | HT | 45 | 2 | 0 | 0.0426 | 1.000 |
| | | NT | 112 | 1 | 0 | 0.0088 | 1.000 |
| | rs1802376 | | GG | GA | AA | | |
| | | HT | 45 | 2 | 0 | 0.0426 | 1.000 |
| | | NT | 111 | 2 | 0 | 0.0177 | 1.000 |
| | rs34910981 | | del del | ins del | ins ins | | |
| | | HT | 44 | 2 | 0 | 0.0435 | 1.000 |
| | | NT | 109 | 2 | 0 | 0.0180 | 1.000 |
| SNX5 | rs6045116 | | GG | GA | AA | | |
| | | HT | 37 | 0 | 0 | 0 | 1.000 |
| | | NT | 119 | 1 | 0 | 0.0042 | 1.000 |
| SNX19 | rs3751037 | | CC | GC | GG | | |
| | | HT | 27 | 17 | 2 | 0.2283 | 0.5484 |
| | | NT | 52 | 45 | 11 | 0.3102 | 0.6809 |
| | rs3190345 | | AA | GA | GG | | |
| | | HT | 30 | 13 | 4 | 0.2234 | 0.3497 |
| | | NT | 64 | 37 | 11 | 0.2634 | 0.06756 |
| | rs681982 | | AA | AC | CC | | |
| | | HT | 44 | 2 | 0 | 0.0435 | 1.000 |
| | | NT | 108 | 2 | 0 | 0.0182 | 1.000 |
| | rs4414223 | | CC | TC | TT | | |
| | | HT | 21 | 22 | 1 | 0.2727 | 1.000 |
| | | NT | 36 | 48 | 16 | 0.4000 | 0.7043 |
| | rs2298566 | | AA | AC | CC | | |
| | | HT | 1 | 19 | 25 | 0.2333 | 0.1188 |
| | | NT | 7 | 50 | 50 | 0.2991 | 0.5130 |

TABLE S3

Distribution of Genotypes in Salt-Sensitive and Salt Resistant Subjects in the UVA Cohort

| Gene | SNP | | Genotypes | | | MAF | HWE |
|---|---|---|---|---|---|---|---|
| CYP11β2 | rs1799998 | | CC | CT | TT | | |
| | | SS | 9 | 17 | 5 | 0.4355 | 0.5207 |
| | | SR | 35 | 64 | 27 | 0.4683 | 0.8225 |
| ADD1 | rs4961 | | GG | GT | TT | | |
| | | SS | 21 | 10 | 0 | 0.1613 | 0.2909 |
| | | SR | 74 | 52 | 0 | 0.2063 | 0.252 |
| | rs1541582 | | AA | AT | TT | | |
| | | SS | 21 | 8 | 1 | 0.1667 | 1.000 |
| | | SR | 67 | 47 | 7 | 0.2521 | 0.7401 |
| AGT | rs699 | | CC | TC | TT | | |
| | | SS | 10 | 13 | 7 | 0.4500 | 0.495 |
| | | SR | 58 | 50 | 21 | 0.3566 | 0.07772 |
| AGTR1 | rs5186 | | AA | CA | CC | | |
| | | SS | 13 | 16 | 2 | 0.3226 | 0.4357 |
| | | SR | 48 | 61 | 15 | 0.3669 | 0.5122 |
| ACE | rs1799752 | | long long | long short | short short | | |
| | | SS | 6 | 20 | 5 | 0.4839 | 0.1044 |
| | | SR | 37 | 70 | 20 | 0.4331 | 0.1675 |
| CAV | rs3807990 | | CC | CT | TT | | |
| | | SS | 15 | 12 | 2 | 0.2759 | 1.000 |
| | | SR | 73 | 42 | 6 | 0.2231 | 0.9896 |
| | rs3840634 | | del del | ins del | ins ins | | |
| | | SS | 17 | 12 | 0 | 0.2069 | 0.3043 |
| | | SR | 77 | 44 | 0 | 0.1818 | 1.000 |
| CCKAR | rs41267457 | | GG | GA | AA | | |
| | | SS | 30 | 1 | 0 | 0.0161 | 1.000 |
| | | SR | 128 | 2 | 0 | 0.0077 | 1.000 |
| CCKBR | rs1805000 | | CC | CT | TT | | |
| | | SS | 30 | 0 | 0 | 0.000 | 1.000 |
| | | SR | 124 | 2 | 0 | 0.0080 | 0.02367 |
| | rs1805002 | | GG | GA | AA | | |
| | | SS | 27 | 4 | 0 | 0.0645 | 1.000 |
| | | SR | 120 | 9 | 0 | 0.0349 | 1.000 |
| CYP4A11 | rs1126742 | | TT | CT | CC | | |
| | | SS | 22 | 9 | 0 | 0.1452 | 1.000 |
| | | SR | 88 | 39 | 0 | 0.1535 | 1.000 |
| DRD2 | rs1799732 | | del del | ins del | ins ins | | |
| | | SS | 22 | 5 | 0 | 0.0926 | 1.000 |
| | | SR | 108 | 19 | 0 | 0.0748 | 0.5557 |
| | rs1800497 | | CC | TC | TT | | |
| | | SS | 18 | 8 | 3 | 0.2414 | 0.2979 |
| | | SR | 72 | 48 | 7 | 0.2441 | 0.7851 |
| | rs1079597 | | AA | GA | GG | | |
| | | SS | 20 | 10 | 1 | 0.1935 | 1.000 |
| | | SR | 82 | 40 | 6 | 0.2031 | 0.6947 |
| | rs6276 | | AA | AG | GG | | |
| | | SS | 10 | 18 | 1 | 0.3448 | 0.09623 |
| | | SR | 69 | 44 | 13 | 0.2778 | 0.1455 |
| GRK4 | rs2960306 | | GG | GT | TT | | |
| | | SS | 16 | 8 | 10 | 0.4118 | 0.002711 |
| | | SR | 56 | 73 | 22 | 0.3874 | 0.8199 |
| | rs1024323 | | CC | CT | TT | | |
| | | SS | 14 | 12 | 8 | 0.4118 | 0.1135 |
| | | SR | 55 | 72 | 24 | 0.3974 | 0.9569 |
| | rs1801058 | | CC | CT | TT | | |
| | | SS | 13 | 14 | 7 | 0.4118 | 0.3818 |
| | | SR | 47 | 72 | 32 | 0.4503 | 0.6506 |
| eNOS | rs1799983 | | GG | TG | TT | | |
| | | SS | 13 | 12 | 5 | 0.3667 | 0.4485 |
| | | SR | 55 | 60 | 8 | 0.3089 | 0.1142 |
| PPP2R2C | rs35368770 | | GG | GA | AA | | |
| | | SS | 31 | 0 | 0 | 0.000 | 1.000 |
| | | SR | 124 | 2 | 0 | 0.0080 | 1.000 |
| | rs35410672 | | CC | CT | TT | | |
| | | SS | 31 | 0 | 0 | 0.000 | 1.000 |
| | | SR | 126 | 2 | 0 | 0.0078 | 1.000 |
| | rs3796403 | | AA | GA | GG | | |
| | | SS | 9 | 16 | 5 | 0.4333 | 0.6377 |
| | | SR | 38 | 69 | 18 | 0.4200 | 0.137 |
| | rs11545013 | | CC | AC | AA | | |
| | | SS | 30 | 0 | 0 | 0.000 | 1.000 |
| | | SR | 127 | 1 | 0 | 0.0039 | 1.000 |

TABLE S3-continued

Distribution of Genotypes in Salt-Sensitive and Salt Resistant Subjects in the UVA Cohort

| Gene | SNP | | Genotypes | | MAF | HWE |
|---|---|---|---|---|---|---|
| SLC4A5 | rs7571842 | | AA | GA | GG | | |
| | | SS | 18 | 11 | 2 | 0.2419 | 1.000 |
| | | SR | 30 | 65 | 34 | 0.5155 | 0.9211 |
| | rs10177833 | | AA | AC | CC | | |
| | | SS | 17 | 11 | 0 | 0.1964 | 0.5488 |
| | | SR | 29 | 65 | 28 | 0.4959 | 0.4684 |
| SNX1 | rs1130604 | | CC | TC | TT | | |
| | | SS | 30 | 0 | 0 | 0.000 | 1.000 |
| | | SR | 127 | 3 | 0 | 0.0115 | 1.000 |
| | rs1802376 | | GG | GA | AA | | |
| | | SS | 31 | 0 | 0 | 0.000 | 1.000 |
| | | SR | 125 | 4 | 0 | 0.0155 | 1.000 |
| | rs34910981 | | del del | ins del | ins ins | | |
| | | SS | 28 | 2 | 0 | 0.0333 | 1.000 |
| | | SR | 125 | 2 | 0 | 0.0079 | 1.000 |
| SNX5 | rs6045116 | | GG | GA | AA | | |
| | | SS | 30 | 0 | 0 | 0.000 | 1.000 |
| | | SR | 126 | 1 | 0 | 0.0039 | 1.000 |
| SNX19 | rs3751037 | | GG | GC | GG | | |
| | | SS | 28 | 2 | 0 | 0.0333 | 1.000 |
| | | SR | 125 | 2 | 0 | 0.0079 | 0.779 |
| | rs3190345 | | AA | GA | GG | | |
| | | SS | 17 | 9 | 5 | 0.3065 | 0.0922 |
| | | SR | 77 | 41 | 10 | 0.2383 | 0.1833 |
| | rs681982 | | AA | AC | CC | | |
| | | SS | 28 | 1 | 0 | 0.0172 | 1.000 |
| | | SR | 124 | 3 | 0 | 0.0118 | 1.000 |
| | rs4414223 | | CC | TC | TT | | |
| | | SS | 13 | 11 | 3 | 0.3148 | 1.000 |
| | | SR | 44 | 59 | 14 | 0.3718 | 0.3897 |
| | rs2298566 | | AA | AC | CC | | |
| | | SS | 16 | 12 | 1 | 0.2414 | 1.000 |
| | | SR | 59 | 57 | 7 | 0.2886 | 0.154 |

The disclosures of each and every patent, patent application, and publication cited herein are hereby incorporated by reference in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Kanbay M, Chen Y, Solak Y, Sanders P W. Mechanisms and consequences of salt sensitivity and dietary salt intake. Curr Opin Nephrol Hypertens. 2011; 20:37-43
2. Sanada H, Jones J E, Jose P A. Genetics of salt-sensitive hypertension. Curr Hypertens Rep. 2011; 13:55-66
3. Morimoto A, Uzu T, Fujii T, Nishimura M, Kuroda S, Nakamura S, Inenaga T, Kimura G. Sodium sensitivity and cardiovascular events in patients with essential hypertension. Lancet. 1997; 350:1734-1737
4. Weinberger M H, Fineberg N S, Fineberg S E, Weinberger M. Salt sensitivity, pulse pressure, and death in normal and hypertensive humans. Hypertension. 2001; 37:429-432
5. Weinberger M H. Salt sensitivity is associated with an increased mortality in both normal and hypertensive humans. J Clin Hypertens (Greenwich). 2002; 4:274-276
6. Weinberger M H, Fineberg N S. Sodium and volume sensitivity of blood pressure. Age and pressure change over time. Hypertension. 1991; 18:67-71
7. Weinberger M H, Miller J Z, Luft F C, Grim C E, Fineberg N S. Definitions and characteristics of sodium sensitivity and blood pressure resistance. Hypertension. 1986; 8:II127-134
8. Weinberger M H. Pathogenesis of salt sensitivity of blood pressure. Curr Hypertens Rep. 2006; 8:166-170
9. Miller J Z, Weinberger M H, Christian J C, Daugherty S A. Familial resemblance in the blood pressure response to sodium restriction. Am J Epidemiol. 1987; 126:822-830
10. Svetkey L P, McKeown S P, Wilson A F. Heritability of salt sensitivity in black Americans. Hypertension. 1996; 28:854-858
11. Beeks E, Kessels A G, Kroon A A, van der Klauw M M, de Leeuw P W. Genetic predisposition to salt-sensitivity: A systematic review. J Hypertens. 2004; 22:1243-1249
12. Miller J Z, Weinberger M H, Christian J C, Daugherty S A. Familial resemblance in the blood pressure response to sodium restriction. Am J Epidemiol. 1987; 126:822-830
13. Boron W F. Acid-base transport by the renal proximal tubule. J Am Soc Nephrol. 2006; 17:2368-2382
14. Skelton L A, Boron W F, Zhou Y. Acid-base transport by the renal proximal tubule. J Nephrol. 2010; 23 Suppl 16:S4-18
15. Rice T, Rankinen T, Chagnon Y C, Province M A, Perusse L, Leon A S, Skinner J S, Wilmore J H, Bouchard C, Rao D C. Genomewide linkage scan of resting blood pressure: HERITAGE Family Study. Health, risk factors, exercise training, and genetics. Hypertension. 2002; 39:1037-1043
16. Hunt S C, Xin Y, Wu L L, Cawthon R M, Coon H, Hasstedt S J, Hopkins P N. Sodium bicarbonate cotransporter polymorphisms are associated with baseline and 10-year follow-up blood pressures. Hypertension. 2006; 47:532-536
17. Stutz A M, Teran-Garcia M, Rao D C, Rice T, Bouchard C, Rankinen T. Functional identification of the promoter of SLC4A5, a gene associated with cardiovascular and metabolic phenotypes in the HERITAGE Family Study. Eur J Hum Genetics. 2009; 17:1481-1489
18. Taylor J Y, Maddox R, Wu C Y. Genetic and environmental risks for high blood pressure among African American mothers and daughters. Biol Res Nurs. 2009; 11:53-65
19. Chamarthi B, Williams J S, Williams G H. A mechanism for salt-sensitive hypertension: abnormal dietary sodium-mediated vascular response to angiotensin-II. J Hypertens. 2010; 28:1020-1026.
20. Pojoga L, Underwood P C, Goodarzi, M, Williams J S, Adler G K, Jeunemaitre X, Hopkins P N, Raby B A, Lasky-Su J, Sun B, Cui J, Guo X, Taylor K D, Chen Y D, Xiang A, Raffel L J, Buchanan T A, Rotter J I, Williams G H. Variants of the caveolin-1 gene: a translational investigation linking insulin resistance and hypertension. J Clin Endocrinol Metab. 2011; 96: 1288-1292.
21. Underwood P C, Chamarthi B, Williams J S, Sun B, Vaidya A, Raby B A, Lasky, Sun J, Hopkins P N, Adler G K, Williams G H. Replication and meta-analysis of a gene-environment interaction between body mass index and the interleukin-6 promoter polymorphism with higher insulin resistance. Metabolism 2011 e-pub
22. Hawkins J R, Khripin Y, Valdes A M, Weaver T A. Miniaturized sealed-tube allele-specific pcr. Hum Mutat. 2002; 19:543-553

23. Shi H, Medway C, Brown K, Kalsheker N, Morgan K. Using Fisher's method with plink 'ld clumped' output to compare snp effects across genome-wide association study (GWAS) datasets. Int J Mol Epidemiol Genet. 2011; 2:30-35
24. Willer C J, Li Y, Abecasis G R. METAL: fast and efficient meta-analysis of genomewide association scans. Bioinformatics. 2010; 26:2190-1.
25. Wain L V, et al., Genome-wide association study identifies six new loci influencing pulse pressure and mean arterial pressure. Nat Genet. 2011; 43:1131-1138.
26. Moore J H, Williams S M. New strategies for identifying gene-gene interactions in hypertension. Ann Med. 2002; 34:88-95
27. Rhee M Y, Yang S J, Oh S W, Park Y, Kim C I, Park H K, Park S W, Park C Y. Novel genetic variations associated with salt sensitivity in the Korean population. Hypertens Res. 2011; 34:606-611
28. Wang Y, O'Connell J R, McArdle P F, Wade J B, Dorff S E, Shah S J, Shi X, Pan L, Rampersaud E, Shen H, Kim J D, Subramanya A R, Steinle N I, Parsa A, Ober C C, Welling P A, Chakravarti A, Weder A B, Cooper R S, Mitchell B D, Shuldiner A R, Chang Y P. From the cover: Whole-genome association study identifies STK39 as a hypertension susceptibility gene. Proc Nat Acad Sci USA. 2009; 106:226-231
29. Sanada H, Yatabe J, Midorikawa S, Hashimoto S, Watanabe T, Moore J H, Ritchie M D, Williams S M, Pezzullo J C, Sasaki M, Eisner G M, Jose P A, Felder R A. Single-nucleotide polymorphisms for diagnosis of salt-sensitive hypertension. Clin Chem. 2006; 52:352-360
30. Bengra C, Mifflin T E, Khripin Y, Manunta P, Williams S M, Jose P A, Felder R A. Genotyping of essential hypertension single-nucleotide polymorphisms by a homogeneous PCR method with universal energy transfer primers. Clin Chem. 2002; 48:2131-2140
31 Caprioli J, Mele C, Mossali C, Gallizioli L, Giacchetti G, Noris M, Remuzzi G, Benigni A. Polymorphisms of EDNRB, AGT, and ACE genes in salt-sensitive hypertension. Can J Physiol Pharmacol. 2008; 86:505-510
32. Pushkin A, Abuladze N, Newman D, Lee I, Xu G, Kurtz I. Cloning, characterization and chromosomal assignment of NBC4, a new member of the sodium bicarbonate cotransporter family. Biochim Biophys Acta. 2000; 1493: 215-218.
33. Rice T, Cooper R S, Wu X, Bouchard C, Rankinen T, Rao D C, Jaquish C E, Fabsitz R R, Province M A. Meta-analysis of genome-wide scans for blood pressure in African American and Nigerian samples. The National Heart, Lung, and Blood Institute genelink project. Am J Hypertens. 2006; 19:270-274
34. Cooper R S, Luke A, Zhu X, Kan D, Adeyemo A, Rotimi C, Bouzekri N, Ward R. Genome scan among Nigerians linking blood pressure to chromosomes 2, 3, and 19. Hypertension. 2002; 40:629-633
35. Barkley R A, Chakravarti A, Cooper R S, Ellison R C, Hunt S C, Province M A, Turner S T, Weder A B, Boerwinkle E. Positional identification of hypertension susceptibility genes on chromosome 2. Hypertension. 2004; 43:477-482
36. Aalkjaer C, Frische S, Leipziger J, Nielsen S, Praetorius J. Sodium coupled bicarbonate transporters in the kidney: an update. Acta Physiol Scand. 2004; 181:505-512
37. Abuladze N, Pushkin A, Tatishchev S, Newman D, Sassani P, Kurtz I. Expression and localization of rat NBC4C in liver and renal uroepithelium. Am J Physiol. Cell Physiol. 2004; 287:C781-789
38. Xu J, Wang Z, Barone S, Petrovic M, Amlal H, Conforti L, Petrovic S, Solcimani M. Expression of the Na+-HCO3-cotransporter NBC4 in rat kidney and characterization of a novel NBC4 variant. Am J Physiol Renal Physiol. 2003; 284:F41-F50.
39. Damkier H H, Nielsen S, Praetorius S. Molecular expression of SLC4-derived Na+-dependent anion transporters in selected tissues. Am J Physiol Renal Physiol. 2007; 293:82136-82146.
40. Groger N, Vitzhum H, Frohlich H, Kruger M, Ehmke H, Braun T, Boettger T. Targeted mutation of SLC4A5 induces arterial hypertension and renal metabolic acidosis. Hum Mol Genet. 2012; 21:1025-1036; electronically published Nov. 14, 2011.
41. Padmanabhan S, Wallace C, Munroe P B, Dobson R, Brown M, Samani N, Clayton D, Farrall M, Webster J, Lathrop M, Caulfield M, Domiczak A F, Connell J M. Chromosome 2p shows significant linkage to antihypertensive response in the British Genetics of Hypertension Study. Hypertension. 2006: 47:603-608.
42. Williams et al., October, 2011, J. Hypertension, 29:10: 1913-1918;

What is claimed is:

1. A method for determining salt sensitivity of blood pressure in a subject, said method comprising determining whether said subject has at least one single nucleotide polymorphism associated with salt sensitivity of blood pressure, wherein a sample from said subject is analyzed and detection of said at least one single nucleotide polymorphism in said sample is an indication of salt sensitivity in said subject, wherein at least one of said single nucleotides polymorphisms is rs7571842 or rs10177833 of the sodium bicarbonate co-transporter gene (SLC4A5), thereby determining salt sensitivity of blood pressure in said subject.

2. The method of claim 1, wherein said at least one single nucleotide polymorphism is detected by genotyping a nucleic acid in said sample.

3. The method of claim 2, wherein two or more single nucleotide polymorphisms are analyzed in said subject and said single nucleotide polymorphisms are selected from the group consisting of
rs1799998,
rs4961,
rs1541582,
rs699,
rs5186,
rs1799752,
rs3807990,
rs3840634,
rs41267457,
rs1805000,
rs1805002,
rs1126742,
rs1799732,
rs1800497,
rs1079597,
rs6276,
rs2960306,
rs1024323,
rs1801058,
rs1799983,
rs35368770,
rs35410672,
rs3796403,
rs11545013,
rs7571842,
rs10177833, rs1130604,
rs1802376,
rs34910981,
rs6045116,
rs3751037,
rs3190345,
rs681982,
rs4414223, and
rs2298566.

4. The method of claim 3, wherein an A allele for rs7571842 is an indication of salt sensitivity of blood pressure in said subject.

5. The method of claim 4, wherein the SLC4A5 gene has the AA or GA genotype of rs7571842.

6. The method of claim 3, wherein an A allele for rs10177833 is an indication of salt sensitivity of blood pressure in said subject.

7. The method of claim 6, wherein the SLC4A5 gene has the AA or AC genotype of rs10177833.

8. The method of claim 3, wherein a C allele for rs1801058 is detected and is an indication of salt sensitivity of blood pressure in said subject.

9. The method of claim 8, wherein the GRK4 gene has the CC or CT genotype of rs1801058.

10. The method of claim 1, wherein rs7571842 and rs10177833 are detected and when subjected to logistic regression analysis rs7571842 has a P value of $1.04 \times 10^{-4}$ and an odds ratio of 0.221 and rs10177833 has a P value of $3.1 \times 10^{-4}$ and an odds ratio of 0.221.

11. The method of claim 1, wherein said subject is hypertensive.

12. The method of claim 1, wherein said subject is normotensive.

13. The method of claim 1, wherein a SNP is genotyped using a fluorescent allele-specific polymerase chain reaction (PCR)-based assay.

14. The method of claim 1, wherein said at least one single nucleotide polymorphism is detected in a sample obtained from said subject and said sample comprises nucleic acids.

15. The method of claim 1, wherein said sample is selected from the group consisting of normal tissue samples, diseased tissue samples, sputum, mucus, phlegm, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, exosomes, and urine.

16. The method of claim 1, wherein said salt sensitivity of blood pressure is determined using a computer-readable medium having computer executable instructions for determining the existence of said salt sensitivity, the computer readable medium comprising: allelic frequency data indicative of at least one polymorphic marker; and a routine stored on the computer readable medium and adapted to be executed by a processor to determine the existence of salt sensitivity of blood pressure.

17. A method for treating a subject susceptible to salt sensitivity of blood pressure, said method comprising determining whether the subject has at least one single nucleotide polymorphism associated with salt sensitivity of blood pressure, wherein a sample from said subject is analyzed and detection of said at least one single nucleotide polymorphism in said sample is an indication of salt sensitivity in said subject, wherein at least one of said at least one single nucleotide polymorphisms is a variant of SLC4A5 and said single nucleotide polymorphisms are selected from the group consisting of
rs1799998,
rs4961,
rs1541582,
rs699,
rs5186,
rs1799752,
rs3807990,
rs3840634,
rs41267457,
rs1805000,
rs1805002,
rs1126742,
rs1799732,
rs1800497,
rs1079597,
rs6276,
rs2960306,
rs1024323,
rs1801058,
rs1799983,
rs35368770,
rs35410672,
rs3796403,
rs11545013,
rs7571842,
rs10177833,
rs1130604,
rs1802376,
rs34910981,
rs6045116,
rs3751037,
rs3190345,
rs681982,
rs4414223, and
rs2298566,
developing a treatment strategy for said subject and administering to said subject a pharmaceutical composition comprising an effective amount of at least one drug useful for treating high blood pressure.

18. The method of claim 17, wherein at least one single nucleotide polymorphism is selected from GRK4.

19. The method of claim 18, wherein said at least one single nucleotide polymorphism is rs1801058.

20. The method of claim 19, wherein a risk allele for rs7571842 is A and a protective allele is G.

21. The method of claim 19, wherein a risk allele for rs10177833 is A and a protective allele is C.

22. The method of claim 17, further wherein said drug is selected from the group consisting of diuretics, mineralocorticoid receptor antagonists, combination diuretics, beta-blockers, alpha-blockers, angiotensin-converting enzyme inhibitors, angiotensin II receptor blockers, calcium channel blockers, central agonists, peripheral acting adrenergic blockers, direct vasodilators, and direct renin inhibitors.

23. The method of claim 17, wherein the salt sensitivity to blood pressure comprises an increase in mean arterial pressure of ≥7.0 mmHg when said subject is tested during a transition from a low to a high sodium diet or said subject has such a change when consuming increased amounts of sodium.

24. The method of claim 23, wherein the salt sensitivity to blood pressure comprises an increase in mean arterial pressure of ≥10.0 mmHg when said subject is tested during a transition from a low to a high sodium diet or said subject has such a change when consuming increased amounts of sodium.

25. The method of claim 17, further wherein said treatment includes providing advice to said subject to reduce their daily, weekly, or monthly salt consumption below the level of their personal salt index.

26. The method of claim 1, wherein when said salt sensitivity of blood pressure is determined in said subject a treatment strategy is developed comprising administering to said subject a pharmaceutical composition comprising an effective amount of at least one drug useful for treating high blood pressure and providing advice to said subject to reduce daily, weekly, or monthly salt consumption below the level of said subject's personal salt index.

* * * * *